(12) United States Patent
Clark et al.

(10) Patent No.: US 6,562,851 B2
(45) Date of Patent: May 13, 2003

(54) SUBSTITUTED BICYCLIC COMPOUNDS

(75) Inventors: David Edward Clark, Brentwood (GB); Paul Robert Eastwood, Romford (GB); Neil Victor Harris, Tilbury (GB); Clive McCarthy, West Malling (GB); Andrew David Morley, Macclesfield (GB); Stephen Dennis Pickett, Brentwood (GB)

(73) Assignee: Aventis Pharma Limited, West Malling (GB)

( * ) Notice: Subject to any disclaimer, the term of this patent is extended or adjusted under 35 U.S.C. 154(b) by 0 days.

(21) Appl. No.: 10/002,041

(22) Filed: Nov. 2, 2001

(65) Prior Publication Data

US 2002/0156111 A1 Oct. 24, 2002

Related U.S. Application Data

(63) Continuation of application No. PCT/GB00/01731, filed on May 5, 2000.
(60) Provisional application No. 60/141,471, filed on Jun. 29, 1999.

(30) Foreign Application Priority Data

May 5, 1999 (GB) .............................................. 9910394

(51) Int. Cl.[7] ...................... A61K 31/423; C07D 263/60
(52) U.S. Cl. ........................................ 514/375; 548/222
(58) Field of Search .......................... 514/375; 548/222

(56) References Cited

FOREIGN PATENT DOCUMENTS

| WO | WO9708145 | 3/1997 |
|---|---|---|
| WO | WO9736862 | 10/1997 |
| WO | WO9843962 | 10/1998 |
| WO | WO9910312 | 3/1999 |
| WO | WO9923063 | 5/1999 |
| WO | WO0005224 | 2/2000 |

Primary Examiner—Cecilia Tsang
Assistant Examiner—Andrea D. Small
(74) Attorney, Agent, or Firm—Ronald G. Ort

(57) ABSTRACT

The invention is directed to physiologically active compounds of general formula (I):

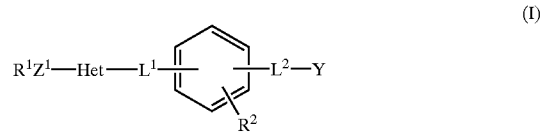

wherein Het is an optionally substituted, saturated, partially saturated or fully unsaturated 8 to 10 membered bicyclic ring system containing at least one heteroatom selected from O, S or N; $R^1$ is optionally substituted aryl, heteroaryl, alkyl, alkenyl, alkynyl, cycloalkyl or heterocycloalkyl; $R^2$ is hydrogen, halogen, lower alkyl or lower alkoxy; $Z^1$ is $NR^5$; $L^1$ is a —$R^6$—$R^7$— linkage (where $R^6$ is alkylene, alkenylene or alkynylene and $R^7$ is a direct bond, cycloalkylene, heterocycloalkylene, aryldiyl, heteroaryldiyl, —C(=$Z^3$)—$NR^5$—, —$NR^5$—C(=$Z^3$)—, —$Z^3$—, —C(=O)—, —C(=$NOR^5$)—, —$NR^5$—, —$NR^5$—C(=$Z^3$)—$NR^5$—, —$SO_2$—$NR^5$—, —$NR^5$—$SO_2$—, —O—C(=O)—, —C(=O)—O—, —$NR^5$—C(=O)—O— or —O—C(=O)—$NR^5$—); $L^2$ is an alkylene chain substituted by hydroxy, oxo, —$OR^4$, —O—C(=O)—$R^4$, —N($R^8$)—C(=O)—$R^9$, —N($R^8$)—C(=O)—$OR^9$, —N($R^8$)—$SO_2$—$R^9$, or —$NY^3Y^4$; and Y is carboxy or an acid bioisostere; and the corresponding N-oxides, and their prodrugs; and pharmaceutically acceptable salts and solvates of such compounds and their N-oxides and prodrugs. Such compounds have valuable pharmaceutical properties, in particular the ability to regulate the interaction of VCAM-1 and fibronectin with the integrin VLA-4 (α4β1).

22 Claims, No Drawings

SUBSTITUTED BICYCLIC COMPOUNDS

This application is a continuation of PCT/GB00/01731, filed May 5, 2000, which claims priority from GB Application No. 9910394.7, filed May 5, 1999, and U.S. Provisional Application No. 60/141,471, filed Jun. 29, 1999; all these applications incorporated herein by reference.

This invention is directed to substituted bicyclic compounds, their preparation, pharmaceutical compositions containing these compounds, and their pharmaceutical use in the treatment of disease states capable of being modulated by the inhibition of cell adhesion.

Cell adhesion is a process by which cells associate with each other, migrate towards a specific target or localise within the extra-cellular matrix. Many of the cell—cell and cell-extracellular matrix interactions are mediated by protein ligands (e.g. fibronectin, VCAM-1 and vitronectin) and their integrin receptors [e.g. α5β1 (VLA-5), α4β1 (VLA-4) and αVβ3]. Recent studies have shown these interactions to play an important part in many physiological (e.g. embryonic development and wound healing) and pathological conditions (e.g. tumour-cell invasion and metastasis, inflammation, atherosclerosis and autoimmune disease).

A wide variety of proteins serve as ligands for integrin receptors. In general, the proteins recognised by integrins fall into one of three classes: extracellular matrix proteins, plasma proteins and cell surface proteins. Extracellular matrix proteins such as collagen fibronectin, fibrinogen, laminin, thrombospondin and vitronectin bind to a number of integrins. Many of the adhesive proteins also circulate in plasma and bind to activated blood cells. Additional components in plasma that are ligands for integrins include fibrinogen and factor X. Cell bound complement C3bi and several transmembrane proteins, such as Ig-like cell adhesion molecule (ICAM-1,2,3) and vascular cell adhesion molecule (VCAM-1), which are members of the Ig superfamily, also serve as cell-surface ligands for some integrins.

Integrins are heterodimeric cell surface receptors consisting of two subunits called α and α. There are at least fifteen different α-subunits (α1-α9, α-L, α-M, α-X, α-IIb, α-V and α-E) and at least seven different β (β1-β7) subunits. The integrin family can be subdivided into classes based on the β subunits, which can be associated with one or more α-subunits. The most widely distributed integrins belong to the β1 class, also known as the very late antigens (VLA). The second class of integrins are leukocyte specific receptors and consist of one of three α-subunits (α-L, -M or α-X) complexed with the β2 protein. The cytoadhesins α-IIbβ3 and α-Vβ3, constitute the third class of integrins.

The present invention principally relates to agents which modulate the interaction of the ligand VCAM-1 with its integrin receptor α4β1 (VLA-4), which is expressed on numerous hematopoietic cells and established cell lines, including hematopoietic precursors, peripheral and cytotoxic T lymphocytes, B lymphocytes, monocytes, thymocytes and eosinophils.

The integrin α4β1 mediates both cell—cell and cell-matrix interactions. Cells expressing α4β1 bind to the carboxy-terminal cell binding domain (CS-1) of the extracellular matrix protein fibronectin, to the cytokine-inducible endothelial cell surface protein VCAM-1, and to each other to promote homotypic aggregation. The expression of VCAM-1 by endothelial cells is upregulated by proinflammatory cytokines such as INF-γ, TNF-α, IL-1β and IL-4.

Regulation of α4β1 mediated cell adhesion is important in numerous physiological processes, including T-cell proliferation, B-cell localisation to germinal centres, and adhesion of activated T-cells and eosinophils to endothelial cells. Evidence for the involvement of VLA-4/VCAM-1 interaction in various disease processes such as melanoma cell division in metastasis, T-cell infiltration of synovial membranes in rheumatoid arthritis, autoimmune diabetes, collitis and leukocyte penetration of the blood-brain barrier in experimental autoimmune encephalomyelitis, atherosclerosis, peripheral vascular disease, cardiovascular disease and multiple sclerosis, has been accumulated by investigating the role of the peptide CS-1 (the variable region of fibronectin to which α4β1 binds via the sequence Leu-Asp-Val) and antibodies specific for VLA-4 or VCAM-1 in various in vitro and in vivo experimental models of inflammation. For example, in a Streptococcal cell wall-induced experimental model of arthritis in rats, intravenous administration of CS-1 at the initiation of arthritis suppresses both acute and chronic inflammation (S. M. Wahl et al., J. Clin. Invest., 1994, 94, pages 655–662). In the oxazalone-sensitised model of inflammation (contact hypersensitivity response) in mice, intravenous administration of anti-α4 specific monoclonal antibodies significantly inhibited (50–60% reduction in the ear swelling response) the efferent response (P. L. Chisholm et al. J. Immunol., 1993, 23, pages 682–688). In a sheep model of allergic bronchoconstriction, HP ½, an anti-α4 monoclonal antibody given intravenously or by aerosol, blocked the late response and the development of airway hyperresponsiveness (W. M. Abraham et al. J. Clin. Invest., 1994, 93 pages 776–787).

We have now found a novel group of substituted bicyclic compounds which have valuable pharmaceutical properties, in particular the ability to regulate the interaction of VCAM-1 and fibronectin with the integrin VLA-4 (α4β1).

Thus, in one aspect, the present invention is directed to compounds of general formula (I):

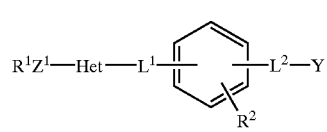

(I)

wherein:

Het represents a saturated, partially saturated or fully unsaturated 8 to 10 membered bicyclic ring system containing at least one heteroatom selected from O, S or N, optionally substituted by one or more aryl group substituents;

$R^1$ represents aryl, heteroaryl, optionally substituted alkyl, alkenyl or alkynyl where each is optionally substituted by $R^3$, —$Z^2R^4$, —$Z^3H$, —C(=O)—$R^4$, —$NR^5$—C(=$Z^3$)—$R^4$, —$NR^5$—C(=O)—$OR^4$, —$NR^5$—$O_2$—$R^4$, —$SO_2$—$NY^1Y^2$, —$NY^1Y^2$ or —C(=$Z^3$)—$NY^1Y^2$; or cycloalkyl or heterocycloalkyl, each optionally substituted by $R^4$, —$Z^2R^4$, —$Z^3H$, —C(=O)—$R^4$, —$NR^5$—C(=$Z^3$)—$R^4$, —$NR^5$—C(=O)—$OR^4$, —$NR^5$—$SO_2$—$R^4$, $SO_2NY^1Y^2$, —$NY^1Y^2$ or —C(=$Z^3$)—$NY^1Y^2$;

$R^2$ represents hydrogen, halogen, lower alkyl or lower alkoxy;

$R^3$ represents aryl, cycloalkyl, cycloalkenyl, heteroaryl, or heterocycloalkyl;

$R^4$ represents alkyl, alkenyl, alkynyl, aryl, arylalkyl, arylalkenyl, arylalkynyl, cycloalkyl, cycloalkylalkyl, cycloalkenyl, cycloalkenylalkyl, heteroaryl, heteroarylalkyl, heteroarylalkenyl, heteroarylalkynyl, heterocycloalkyl or heterocycloalkylalkyl;

$R^5$ represents hydrogen or lower alkyl;

$R^6$ is an alkylene chain, an alkenylene chain or an alkynylene chain;

$R^7$ is a direct bond, cycloalkylene, heterocycloalkylene, aryldiyl, heteroaryldiyl, —C(=$Z^3$)—$NR^5$—, —$NR^5$—C(=$Z^3$)—, —$Z^3$—, —C(=O)—, —C(=$NOR^5$)—, —$NR^5$—, —$NR^5$—C(=$Z^3$)—$NR^5$—, —$SO_2$—$NR^5$—, —$NR^5$—$SO_2$—, —O—C(=O)—, —C(=O)—O—, —$NR^5$—C(=O)—O— or —O—C(=O)—$NR^5$—;

$R^8$ is hydrogen, alkyl, aryl, arylalkyl, cycloalkyl, cycloalkylalkyl, heteroaryl, heteroarylalkyl, heterocycloalkyl or heterocycloalkylalkyl;

$R^9$ is alkyl, aryl, cycloalkyl, heteroaryl or heterocycloalkyl, or alkyl substituted by aryl, an acidic functional group or corresponding protected derivative, cycloalkyl, heteroaryl, heterocycloalkyl, —$Z^3$H, —$Z^2R^4$, —C(=O)—$NY^3Y^4$ or —$NY^3Y^4$;

$L^1$ represents a —$R^6$—$R^7$— linkage;

$L^2$ represents an alkylene chain substituted by hydroxy, oxo, —$OR^4$, —O—C(=O)—$R^4$, —N($R^8$)—C(=O)—$R^9$, —N($R^8$)—C(=O)—$OR^9$, —N($R^8$)—$SO_2$—$R^9$, or —$NY^3Y^4$;

Y is carboxy or an acid bioisostere;

$Y^1$ and $Y^2$ are independently hydrogen, alkenyl, alkyl, aryl, arylalkyl, cycloalkyl, heteroaryl or heteroarylalkyl; or the group —$NY^1Y^2$ may form a cyclic amine;

$Y^3$ and $Y^4$ are independently hydrogen, alkenyl, alkyl, alkynyl, aryl, cycloalkenyl, cycloalkyl, heteroaryl, heterocycloalkyl, or alkyl substituted by alkoxy, aryl, cyano, cycloalkyl, heteroaryl, heterocycloalkyl, hydroxy, oxo, —$NY^1Y^2$, or one or more —$CO_2R^8$ or —C(=O)—$NY^1Y^2$ groups; or the group —$NY^3Y^4$ may form a cyclic amine;

$Z^1$ represents $NR^5$;

$Z^2$ is O or S(O)$_n$;

$Z^3$ is O or S; and n is zero or an integer 1 or 2;

and the corresponding N-oxides, and their prodrugs; and pharmaceutically acceptable salts and solvates (e.g. hydrates) of such compounds and their N-oxides and prodrugs; but excluding compounds where an oxygen, nitrogen or sulphur atom is attached directly to a carbon carbon multiple bond of an alkenyl or alkynyl residue.

In the present specification, the term "compounds of the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986, 21, p283 "Bioisosterism In Drug Design"; Yun, Hwahak Sekye, 1993, 33, p576–579 "Application Of Bioisosterism To New Drug Design"; Zhao, Huaxue Tongbao, 1995, p34–38 "Bioisosteric Replacement And Development Of Lead Compounds In Drug Design"; Graham, Theochem, 1995, 343, p105–109 "Theoretical Studies Applied To Drug Design:ab initio Electronic Distributions In Bioisosteres"). Examples of suitable acid bioisosteres include: —C(=O)—NHOH, —C(=O)—$CH_2$OH, —C(=O)—$CH_2$SH, —C(=O)—NH—CN, sulpho, phosphono, alkylsulphonylcarbamoyl, tetrazolyl, arylsulphonylcarbamoyl, heteroarylsulphonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acidic functional group" means a group with an acidic hydrogen within it. The "corresponding protected derivatives" are those where the acidic hydrogen atom has been replaced with a suitable protecting group. For suitable protecting groups see T. W. Greene and P. G. M. Wuts in "Protective Groups in Organic Chemistry" John Wiley and Sons, 1991. Exemplary acidic functional groups include carboxyl (and acid bioisosteres), hydroxy, mercapto and imidazole. Exemplary protected derivatives include esters of carboxy groups, ethers of hydroxy groups, thioethers of mercapto groups and N-benzyl derivatives of imidazoles.

"Acyl" means an H—CO— or alkyl-CO— group in which the alkyl group is as described herein.

"Acylamino" is an acyl-NH— group wherein acyl is as defined herein.

"Alkenyl" means an aliphatic hydrocarbon group containing a carbon—carbon double bond and which may be straight or branched having about 2 to about 15 carbon atoms in the chain. Preferred alkenyl groups have 2 to about 12 carbon atoms in the chain; and more preferably 2 to about 6 carbon atoms (e.g. 2 to 4 carbon atoms) in the chain. "Branched", as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkenylene" means an aliphatic bivalent radical derived from a straight or branched alkenyl group, in which the alkenyl group is as described herein. Exemplary alkenylene radicals include vinylene and propylene.

"Alkoxy" means an alkyl-O— group in which the alkyl group is as described herein. Exemplary alkoxy groups include methoxy, ethoxy, n-propoxy, i-propoxy, n-butoxy and heptoxy.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched having about 1 to about 15 carbon atoms in the chain optionally substituted by alkoxy or by one or more halogen atoms. Particular alkyl groups have from 1 to about 6 carbon atoms. "Lower alkyl" as a group or part of a lower alkoxy, lower alkylthio, lower alkylsulphinyl or lower alkylsulphonyl group means unless otherwise specified, an aliphatic hydrocarbon group which may be straight or branched having 1 to about 4 carbon atoms in the chain. Exemplary alkyl groups include methyl, ethyl, n-propyl, i-propyl, n-butyl, s-butyl, t-butyl, n-pentyl, 3-pentyl, heptyl, octyl, nonyl, decyl and dodecyl.

"Alkylene" means an aliphatic bivalent radical derived from a straight or branched alkyl group, in which the alkyl group is as described herein. Exemplary alkylene radicals include methylene, ethylene and trimethylene.

"Alkylenedioxy" means an —O-alkylene-O— group in which alkylene is as defined above. Exemplary alkylenedioxy groups include methylenedioxy and ethylenedioxy.

"Alkylsulphinyl" means an alkyl-SO— group in which the alkyl group is as previously described. Preferred alkylsulphinyl groups are those in which the alkyl group is $C_{1-4}$alkyl.

"Alkylsulphonyl" means an alkyl-$SO_2$— group in which the alkyl group is as previously described. Preferred alkylsulphonyl groups are those in which the alkyl group is $C_{1-4}$alkyl.

"Alkylsulphonylcarbamoyl" means an alkyl-$SO_2$—NH—C(=O)— group in which the alkyl group is as previously described. Preferred alkylsulphonylcarbamoyl groups are those in which the alkyl group is $C_{1-4}$alkyl.

"Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon—carbon triple bond and which may be straight or branched having about 2 to about 15 carbon atoms in the chain. Preferred alkynyl groups have 2 to about 12 carbon atoms in the chain; and more preferably 2 to about 6 carbon atoms (e.g. 2 to 4 carbon atoms) in the chain. Exemplary alkynyl groups include ethynyl, propynyl, n-butynyl, i-butynyl, 3-methylbut-2-ynyl, and n-pentynyl.

"Alkynylene" means an aliphatic bivalent radical derived from a straight or branched alkynyl group, in which the alkynyl group is as described herein. Exemplary alkynylene radicals include ethynylene and propynylene.

"Aroyl" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Aryl groups may be substituted with one or more aryl group substituents which may be the same or different, where "aryl group substituent" includes, for example, acyl, acylamino, alkoxy, alkoxycarbonyl, alkylenedioxy, alkylsulphinyl, alkylsulphonyl, alkylthio, aroyl, aroylamino, aryl, arylalkyloxy, arylalkyloxycarbonyl, arylalkylthio, aryloxy, aryloxycarbonyl, arylsulphinyl, arylsulphonyl, arylthio, carboxy, cyano, halo, heteroaroyl, heteroaryl, heteroarylalkyloxy, heteroaroylamino, heteroaryloxy, hydroxy, nitro, trifluoromethyl, $Y^1Y^2N$—, $Y^1Y^2NCO$—, $Y^1Y^2NSO_2$—, $Y^1Y^2N$—$C_{2-6}$alkylene-Z—[where Z is O, $NR^5$ or $S(O)_n$], alkylC(=O)—$Y^1N$—, alkyl$SO_2$—$Y^1N$— or alkyl optionally substituted with aryl, heteroaryl, hydroxy, or $Y^1Y^2N$—. When $R^1$ is an optionally substituted aryl group, this may particularly represent optionally substituted phenyl.

"Arylalkenyl" means an aryl-alkenyl— group in which the aryl and alkenyl are as previously described. Preferred arylalkenyls contain a lower alkenyl moiety. Exemplary arylalkenyl groups include styryl and phenylallyl.

"Arylalkyl" means an aryl-alkyl— group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O—CO— group in which the arylalkyl groups is as previously described. An exemplary arylalkyloxycarbonyl group is benzyloxycarbonyl.

"Arylalkylthio" means an arylalkyl—S— group in which the arylalkyl group is as previously described. An exemplary arylalkylthio group is benzylthio.

"Arylalkynyl" means an aryl-alkynyl— group in which the aryl and alkynyl are as previously described. Exemplary arylalkynyl groups include phenylethynyl and 3-phenylbut-2-ynyl.

"Aryldiyl" means an optionally substituted bivalent radical derived from an aryl group. Exemplary aryldiyl groups include optionally substituted phenylene, naphthylene and indanylene. Suitable substituents include one or more "aryl group substituents" as defined above, particularly halogen, methyl or methoxy.

"Aryloxy" means an aryl-O— group in which the aryl group is as previously described. Exemplary aryloxy groups include optionally substituted phenoxy and naphthoxy.

"Aryloxycarbonyl" means an aryl-O—C(=O)— group in which the aryl group is as previously described. Exemplary aryloxycarbonyl groups include phenoxycarbonyl and naphthoxycarbonyl.

"Arylsulphinyl" means an aryl-SO— group in which the aryl group is as previously described.

"Arylsulphonyl" means an aryl-$SO_2$— group in which the aryl group is as previously described.

"Arylsulphonylcarbamoyl" means an aryl-$SO_2$—NH—C(=O)— group in which the aryl group is as previously described.

"Arylthio" means an aryl-S— group in which the aryl group is as previously described. Exemplary arylthio groups include phenylthio and naphthylthio.

"Cyclic amine" means a 3 to 8 membered monocyclic cycloalkyl ring system where one of the ring carbon atoms is replaced by nitrogen and which (i) may be optionally substituted with one or more substituents selected from alkoxy, carboxamido, carboxy, hydroxy, oxo (or a 5-, 6- or 7-membered cyclic acetal derivative thereof) or $R^9$; (ii) may also contain a further heteroatom selected from O, S, $SO_2$, or $NY^5$ (where $Y^5$ is hydrogen, alkyl, aryl, arylalkyl, —C(=O)—$R^{10}$, —C(=O)—$OR^{10}$ or —$SO_2R^{10}$ and $R^{10}$ is alkyl, aryl, arylalkyl, cycloalkyl, cycloalkylalkyl, heteroaryl, heteroarylalkyl, heterocycloalkyl or heterocycloalkylalkyl); and (iii) may be fused to additional aryl (e.g. phenyl), heteroaryl (e.g. pyridyl), heterocycloalkyl or cycloalkyl rings to form a bicyclic or tricyclic ring system. Exemplary cyclic amines include pyrrolidine, piperidine, morpholine, piperazine, indoline, pyrindoline, tetrahydroquinolinyl and the like groups.

"Cycloalkenyl" means a non-aromatic monocyclic or multicyclic ring system containing at least one carbon—carbon double bond and having about 3 to about 10 carbon atoms. Exemplary monocyclic cycloalkenyl rings include cyclopentenyl, cyclohexenyl or cycloheptenyl.

"Cycloalkenylalkyl" means a cycloalkenyl-alkyl— group in which the cycloalkenyl and alkyl moieties are as previously described. Exemplary cycloalkenylalkyl groups include cyclopentenylmethyl, cyclohexenylmethyl or cycloheptenylmethyl.

"Cycloalkyl" means a saturated monocyclic or bicyclic ring system of about 3 to about 10 carbon atoms optionally substituted by oxo. Exemplary monocyclic cycloalkyl rings include $C_{3-8}$cycloalkyl rings such as cyclopropyl, cyclopentyl, cyclohexyl and cycloheptyl.

"Cycloalkylalkyl" means a cycloalkyl-alkyl— group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl.

"Cycloalkylene" means a bivalent radical derived from a cycloalkyl group.

"Halo" or "halogen" means fluoro, chloro, bromo, or iodo. Preferred are fluoro or chloro.

"Heteroaroyl" means a heteroaryl-C(=O)— group in which the heteroaryl group is as described herein. Exemplary groups include pyridylcarbonyl.

"Heteroaroylamino" means a heteroaroyl-NH— group in which the heteroaryl moiety are as previously described.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for example nitrogen, oxygen or sulphur (examples of such groups include benzimidazolyl, benzthiazolyl, furyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above); (ii) an optionally substituted partially saturated multicyclic heterocarbocyclic moiety in which a heteroaryl and a cycloalkyl or cycloalkenyl group are fused together to form a cyclic structure (examples of such groups include pyrindanyl groups). Optional substituents include one or more "aryl group substituents" as defined above.

"Heteroarylalkenyl" means a heteroaryl-alkenyl— group in which the heteroaryl and alkenyl moieties are as previously described. Preferred heteroarylalkenyl groups contain a lower alkenyl moiety. Exemplary heteroarylalkenyl groups include pyridylethenyl and pyridylallyl.

"Heteroarylalkyl" means a heteroaryl-alkyl— group in which the heteroaryl and alkyl moieties are as previously described. Preferred heteroarylalkyl groups contain a $C_{1-4}$alkyl moiety. Exemplary heteroarylalkyl groups include pyridylmethyl.

"Heteroarylalkyloxy" means an heteroarylalkyl-O— group in which the heteroarylalkyl group is as previously described. Exemplary heteroaryloxy groups include optionally substituted pyridylmethoxy.

"Heteroarylalkynyl" means a heteroaryl-alkynyl— group in which the heteroaryl and alkynyl moieties are as previously described. Exemplary heteroarylalkenyl groups include pyridylethynyl and 3-pyridylbut-2-ynyl.

"Heteroaryldiyl" means a bivalent radical derived from a heteroaryl group.

"Heteroaryloxy" means an heteroaryl-O— group in which the heteroaryl group is as previously described. Exemplary heteroaryloxy groups include optionally substituted pyridyloxy.

"Heteroarylsulphonylcarbamoyl" means a heteroaryl-$SO_2$—NH—C(=O)— group in which the heteroaryl group is as previously described.

"Heterocycle" denotes an optionally substituted saturated, partially saturated or fully unsaturated monocyclic organic moiety of 5 or 6 ring members in which one or more of the ring members is/are element(s) other than carbon, for example nitrogen, oxygen or sulphur. Exemplary 5 or 6 membered heterocycles include furyl, imidazolyl, isoxazolyl, isothiazolyl, oxadiazolyl, oxazolyl, oxazinyl, piperidinyl, pyrazinyl, pyridazinyl, pyrazolyl, pyridyl, pyrimidinyl, pyrrolyl, pyrrolidinyl, pyrrolinyl, 1,3,4-thiadiazolyl, thiazolyl, thienyl and triazolyl groups. Optional substituents include one or more "aryl group substituents" as defined above.

"Heterocycloalkyl" means: (i) a cycloalkyl group of about 3 to 7 ring members which contains one or more heteroatoms selected from O, S or $NY^5$ and optionally substituted by oxo; (ii) a partially saturated multicyclic heterocarbocyclic moiety in which an aryl (or heteroaryl ring), each optionally substituted by one or more "aryl group substituents", and a heterocycloalkyl group are fused together to form a cyclic structure (examples of such groups include chromanyl, dihydrobenzofuranyl, indolinyl and pyrindolinyl groups).

"Heterocycloalkylalkyl" means a heterocycloalkyl-alkyl— group in which the heterocycloalkyl and alkyl moieties are as previously described.

"Heterocycloalkylene" means a bivalent radical derived from a heterocycloalkyl group.

"Prodrug" means a compound which is convertible in vivo by metabolic means (e.g. by hydrolysis) to a compound of formula (I), including N-oxides thereof. For example an ester of a compound of formula (I) containing a hydroxy group may be convertible by hydrolysis in vivo to the parent molecule. Alternatively an ester of a compound of formula (I) containing a carboxy group may be convertible by hydrolysis in vivo to the parent molecule.

Suitable esters of compounds of formula (I) containing a hydroxy group, are for example acetates, citrates, lactates, tartrates, malonates, oxalates, salicylates, propionates, succinates, fumarates, maleates, methylene-bis-p-hydroxynaphthoates, gentisates, isethionates, di-p-toluoyltartrates, methanesulphonates, ethanesulphonates, benzenesulphonates, p-toluenesulphonates, cyclohexylsulphamates and quinates.

Suitable esters of compounds of formula (I) containing a carboxy group, are for example those described by F. J. Leinweber, Drug Metab. Res., 1987, 18, page 379.

An especially useful class of esters of compounds of formula (I) containing a hydroxy group, may be formed from acid moieties selected from those described by Bundgaard et. al., J. Med. Chem., 1989, 32 page 2503–2507, and include substituted (aminomethyl)-benzoates, for example dialkylamino-methylbenzoates in which the two alkyl groups may be joined together and/or interrupted 2by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Where the compound of the invention contains a carboxy group, or a sufficiently acidic bioisostere, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) aminomethane, tetramethylammonium hydroxide, and the like.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinates.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (I) above, the following are particular and preferred groupings:

$R^1$ may particularly represent optionally substituted aryl, especially optionally substituted phenyl.

$R^1$ may also particularly represent optionally substituted heteroaryl.

$R^1$ may also particularly represent arylalkyl (e.g. benzyl and phenethyl).

$R^1$ may also particularly represent cycloalkyl (e.g. cyclohexyl).

$Z^1$ may particularly represent NH.

Het may particularly represent

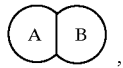, wherein ring

is a 5 or 6 membered heterocycle and ring

is a 5 or 6 membered heterocycle or a benzene ring, each ring optionally substituted by one or more "aryl group substituents" as defined above, and the two rings are joined together by a carbon—carbon linkage or a carbon-nitrogen linkage.

Ring

may particularly represent a 5 membered fully unsaturated heterocycle, optionally substituted by one or more "aryl group substituents" as defined above.

Ring

may particularly represent a benzene ring, optionally substituted by one or more "aryl group substituents" as defined above.

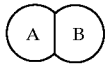

may particularly represent a 9 membered bicyclic system in which rings

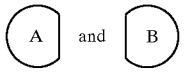

are as defined just above and the two rings are joined together by carbon atom linkages.

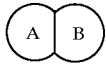

is preferably optionally substituted benzimidazolyl or, more preferably, optionally substituted benzoxazolyl.

Each of rings

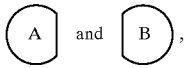, but more particularly ring

B, may be substituted by one or more "aryl group substituents" as defined above [examples of particular aryl group substituents include lower alkyl (e.g. methyl), lower alkoxy (e.g. methoxy), amino, halogen, hydroxy, lower alkylthio, lower alkylsulphinyl, lower alkylsulphonyl, nitro or trifluoromethyl].

$L^1$ may particularly represent a —$R^6$—$R^7$— linkage where $R^6$ represents a straight or branched $C_{1-6}$alkylene chain, especially a straight or branched $C_{1-4}$alkylene chain, and $R^7$ represents —C(=$Z^3$)—N$R^5$—, preferably —C(=O)—N$R^5$—, especially where $R^5$ is hydrogen or lower alkyl (e.g. methyl).

$R^2$ may particularly represent hydrogen.

$R^2$ may also particularly represent lower alkyl (e.g. methyl).

$R^2$ may also particularly represent lower alkoxy (e.g. methoxy)

$L^2$ may particularly represent a straight or branched $C_{1-4}$alkylene chain, especially ethylene, substituted by —N($R^8$)—C(=O)—$R^9$, —N($R^8$)—C(=O)—O$R^9$, —N($R^8$)—SO$_2$—$R^9$, or —N$Y^3Y^4$. $L^2$ is preferably a group

—CH—CH$_2$—,
  |
  $R^{11}$ particularly

—CH—CH$_2$—,
  |
  $R^{11}$ where $R^{11}$ is —N($R^8$)—C(=O)—$R^9$, $R^{11}$ $R^{11}$—N($R^8$)—C(=O)—O$R^9$, —N($R^8$)—SO$_2$—$R^9$, or —N$Y^3Y^4$.

Y may particularly represent carboxy.

It is to be understood that this invention covers all appropriate combinations of the particular and preferred groupings referred to herein.

A particular group of compounds of the invention are compounds of formula (Ia):

(Ia)

$R^1Z^1$— [benzoxazole ring with X, $R^6$, $R^{12}$, positions 5,6] —C(=O)—N($R^5$)—[phenyl with $R^2$]—$L^2$—Y in which $R^1$, $R^2$, $R^5$, $R^6$, $L^2$, Y and $Z^1$ are as defined in any preceding claim, $R^{12}$ is hydrogen, acyl, acylamino, alkoxy, alkoxycarbonyl, alkylenedioxy, alkylsulphinyl, alkylsulphonyl, alkylthio, aroyl, aroylamino, aryl, arylalkyloxy, arylalkyloxycarbonyl, arylalkylthio, aryloxy, aryloxycarbonyl, arylsulphinyl, arylsulphonyl, arylthio, carboxy, cyano, halo, heteroaroyl, heteroaryl, heteroarylalkyloxy, heteroaroylamino, heteroaryloxy, hydroxy, nitro, trifluoromethyl, $Y^1Y^2$N—, $Y^1Y^2$NCO—, $Y_1Y^2$NSO$_2$—, $Y^1Y^2$N—C$_{2-6}$alkylene-Z—, alkylC(=O)—$Y^1$N—, alkylSO$_2$—$Y^1$N— or alkyl optionally substituted with aryl, heteroaryl, hydroxy, or $Y^1Y^2$N—, and X is O, and their prodrugs and pharmaceutically acceptable salts, and solvates (e.g. hydrates) of compounds of formula (Ia) and their prodrugs.

Compounds of formula (Ia) in which $R^1$ represents optionally substituted aryl, especially optionally substituted phenyl, are preferred. Preferred optional substituents include lower alkyl (e.g. methyl), lower alkyl (e.g. methoxy), halo (e.g. fluoro) and $Y^1Y^2$N— (e.g. dimethylamino). $R^1$ especially represents ortho-tolyl.

Compounds of formula (Ia) in which $Z^1$ represents NH are preferred.

Compounds of formula (Ia) in which $R^{12}$ represents hydrogen, $C_{14}$ alkyl or $C_{1-4}$ alkoxy are preferred.

Compounds of formula (Ia) in which $R^6$ represents a straight or branched $C_{1-6}$alkylene chain, especially a straight or branched $C_{1-4}$alkylene chain, more especially methylene, are preferred.

Compounds of formula (Ia) in which $R^5$ represents hydrogen are preferred.

Compounds of formula (Ia) in which $R^2$ represents hydrogen are preferred.

Compounds of formula (Ia) in which $L^2$ represents a straight $C_{1-4}$alkylene chain, especially ethylene, substituted by —N($R^8$)—C(=O)—$R^9$, —N($R^8$)—C(=O)—O$R^9$, —N($R^8$)—SO$_2$—$R^9$ or —N$Y^3Y^4$ are also preferred. Compounds of formula (Ia) in which $L^2$ is a

—CH—CH$_2$—
  |
  $R^{11}$ linkage, particularly

—CH—CH$_2$—,
  |
  $R^{11}$ where $R^{11}$ is —N($R^8$)—C(=O)—$R^9$, —N($R^8$)—C(=O)—O$R^9$, —N($R^8$)—SO$_2$—$R^9$ or —N$Y^3Y^4$ are especially preferred.

Compounds of formula (Ia) in which Y represents carboxy are preferred.

The group

—$R^6$—C(=O)—N($R^5$)—[phenyl with $R^2$]—$L^2$—Y may preferably be attached at the ring 6 position.

A preferred group of compounds of the invention are compounds of formula (Ia) in which: $R^1$ is optionally substituted phenyl (especially ortho-tolyl); $Z^1$ is NH; X is T; $R^6$ is a straight $C_{1-4}$alkylene chain (especially methylene); $R^2$ and $R^5$ and $R^{12}$ are each hydrogen; $L^2$ is a

—CH—CH$_2$—
  |
  $R^{11}$ linkage, particularly

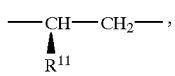

where $R^{11}$ is $-N(R^8)-C(=O)-R^9$, $-N(R^8)-C(=O)-OR^9$, $-N(R^8)-SO_2-R^9$ or $-NY^3Y^4$; Y is carboxy; and the group

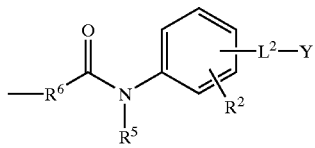

is attached at the ring 6 position; and the corresponding N-oxides, and their prodrugs; and pharmaceutically acceptable salts and solvates (e.g. hydrates) of such compounds and their N-oxides and prodrugs.

Particular compounds of the invention are selected from the compounds formed by joining the acyl carbon atom (C*) of one of the fragments (A1 to A32) shown in Table 1 to the nitrogen atom (N*) of one of the fragments (B1 or B2) shown in Table 2, and joining the carbon atom (C*) of the phenyl ring in one of the fragments (B1 or B2) shown in Table 2 to the carbon atom (C*) of one of the acidic fragments (C1 to C30) depicted in Table 3.

TABLE 1

A1
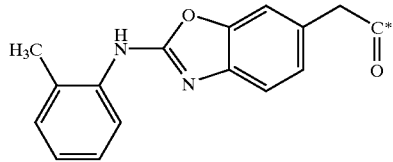

A2
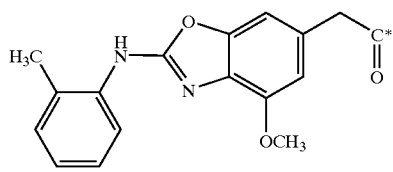

A3
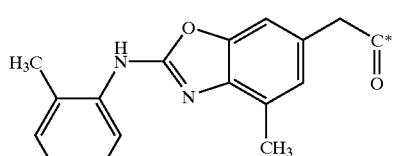

A4
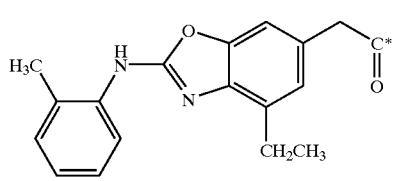

TABLE 1-continued

A5
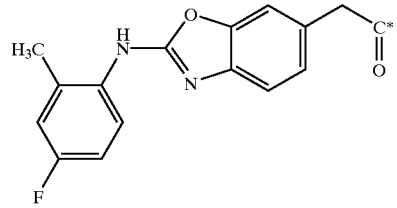

A6
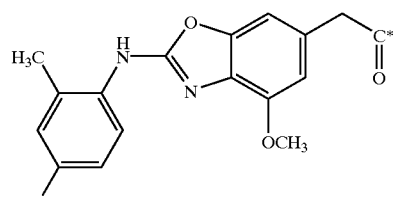

A7
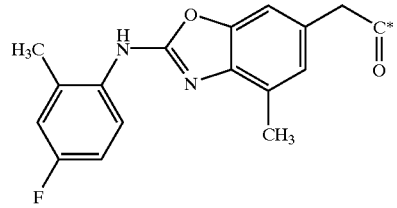

A8
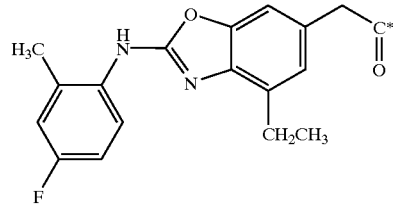

A9
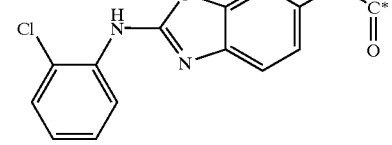

A10
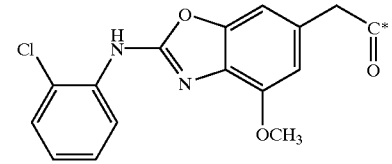

A11
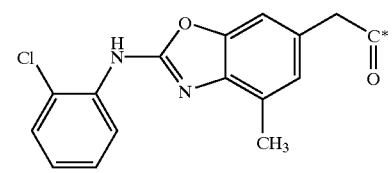

A12
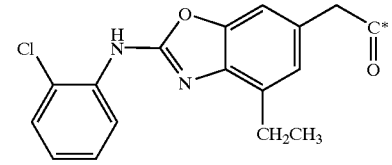

TABLE 1-continued
A13 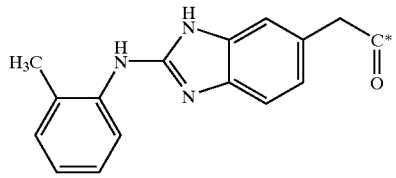
A14 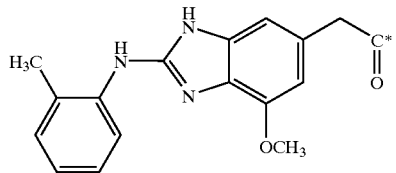
A15 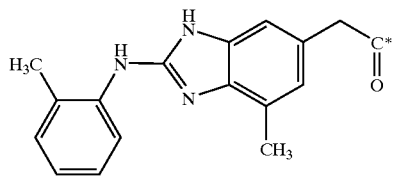
A16 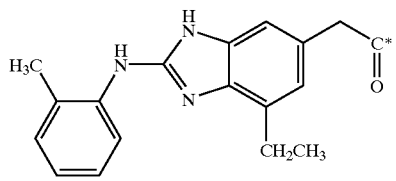
A17 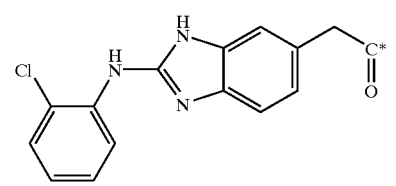
A18 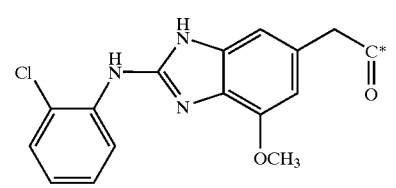
A19 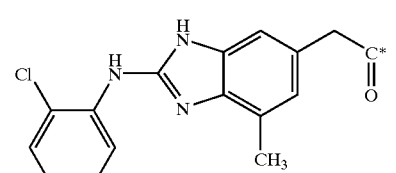
A20 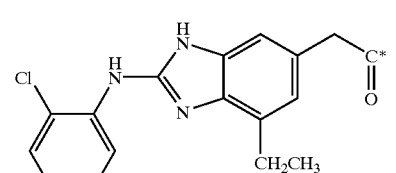
TABLE 1-continued
A21 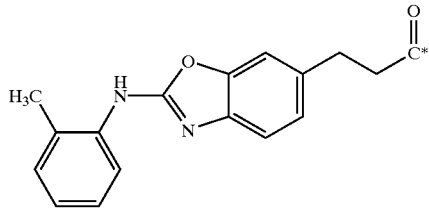
A22 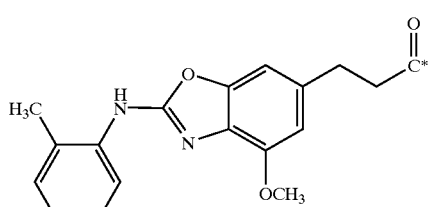
A23 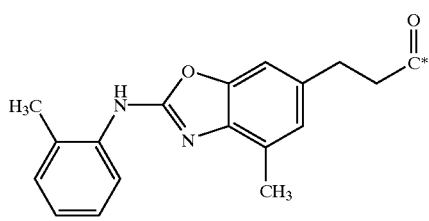
A24 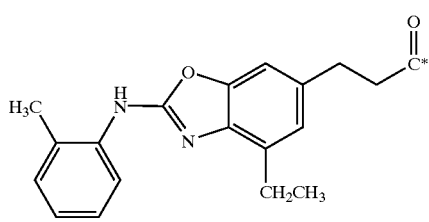
A25 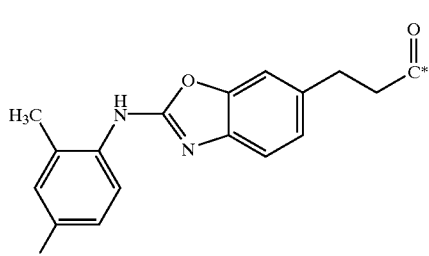
A26 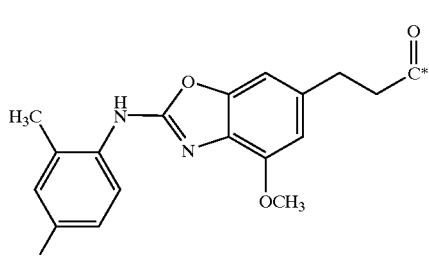

TABLE 1-continued
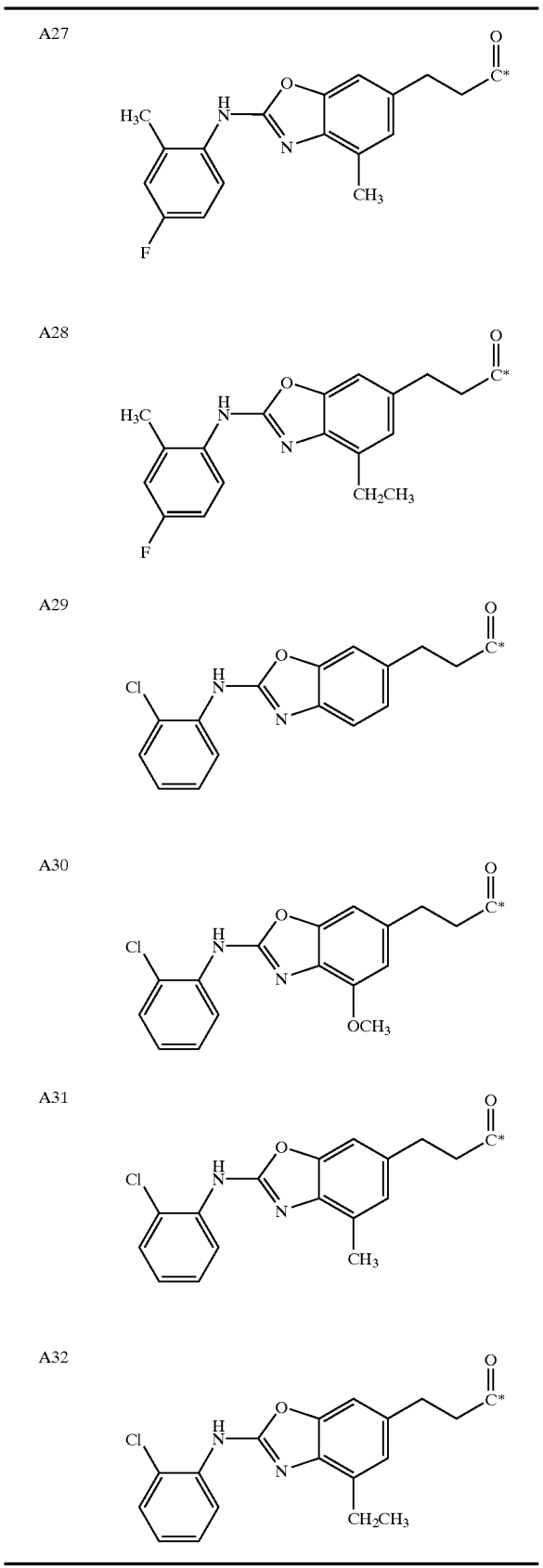
TABLE 2
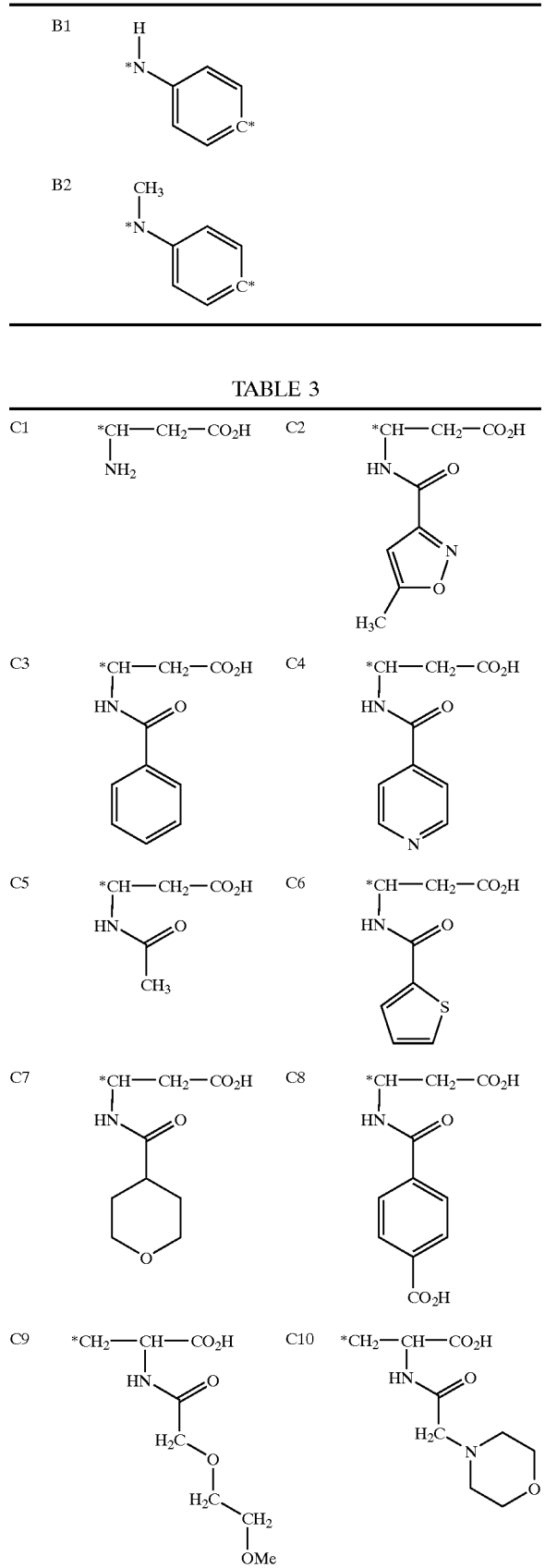

TABLE 3-continued
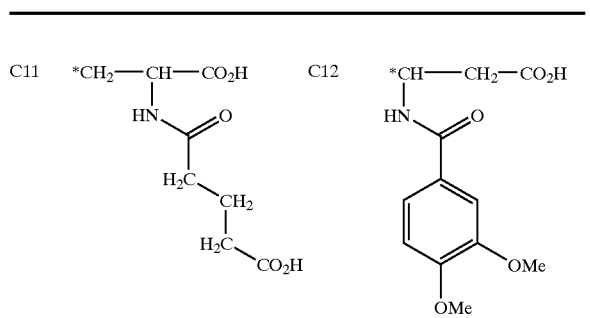
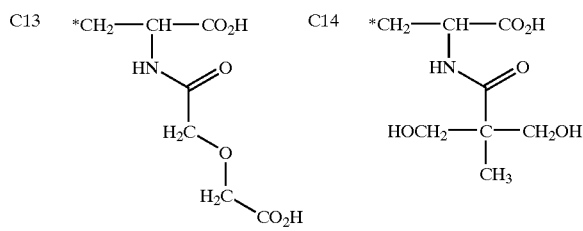
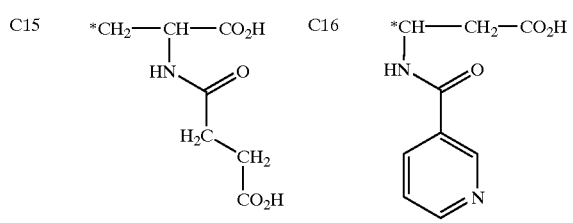
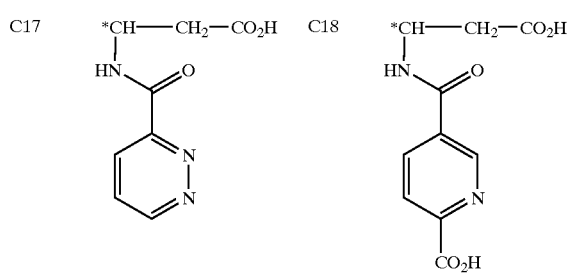
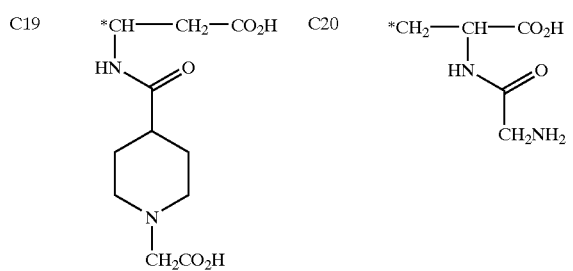
TABLE 3-continued
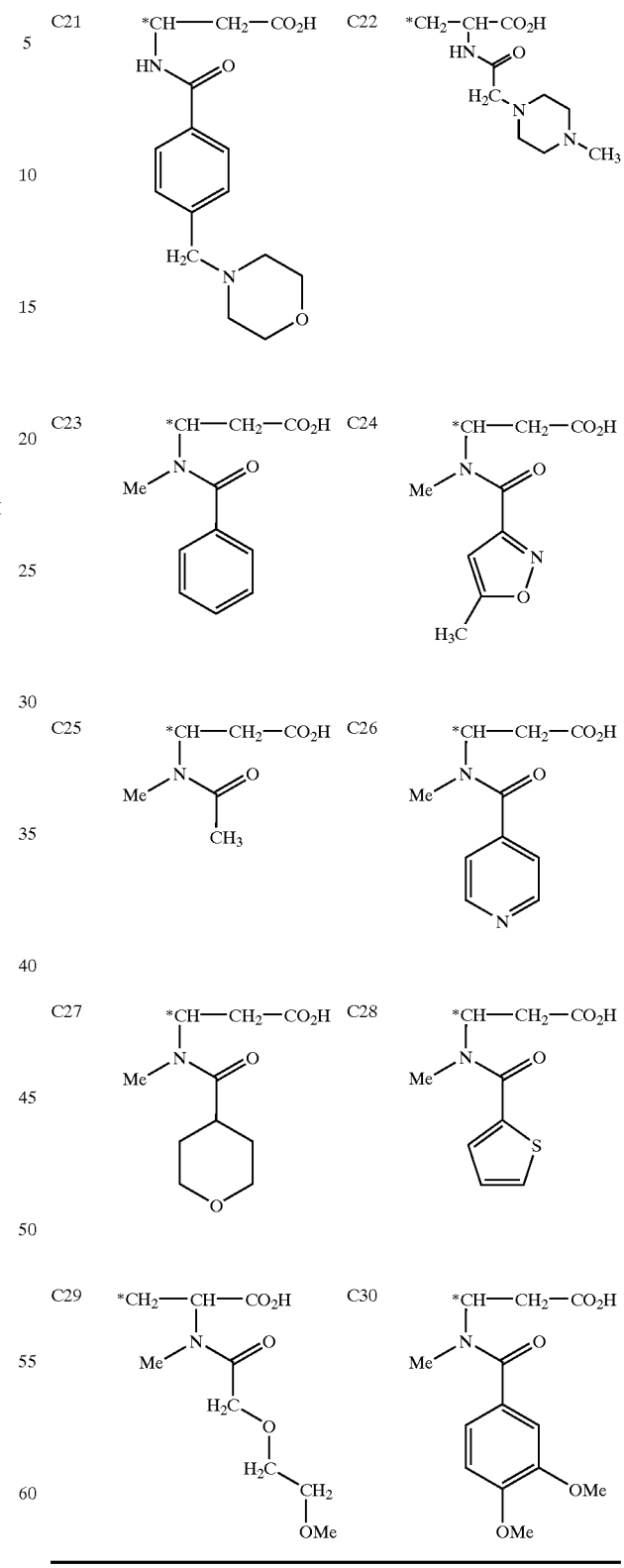
Particularly preferred examples of fragments "A", "B", and "C" are illustrated below:

| | | | | | |
|---|---|---|---|---|---|
| A1-B1-C1; | A1-B1-C6; | A1-B1-C11; | A1-B1-C16; | A1-B1-C21; | A1-B1-C26; |
| A1-B1-C2; | A1-B1-C7; | A1-B1-C12; | A1-B1-C17; | A1-B1-C22; | A1-B1-C27; |
| A1-B1-C3; | A1-B1-C8; | A1-B1-C13; | A1-B1-C18; | A1-B1-C23; | A1-B1-C28; |
| A1-B1-C4; | A1-B1-C9; | A1-B1-C14; | A1-B1-C19; | A1-B1-C24; | A1-B1-C29; |
| A1-B1-C5; | A1-B1-C10; | A1-B1-C15; | A1-B1-C20; | A1-B1-C25; | A1-B1-C30; |
| A2-B1-C1; | A3-B1-C6; | A4-B1-C11; | A5-B1-C16; | A6-B1-C21; | A7-B1-C26; |
| A2-B1-C2; | A3-B1-C7; | A4-B1-C12; | A5-B1-C17; | A6-B1-C22; | A7-B1-C27; |
| A2-B1-C3; | A3-B1-C8; | A4-B1-C13; | A5-B1-C18; | A6-B1-C23; | A7-B1-C28; |
| A2-B1-C4; | A3-B1-C9; | A4-B1-C14; | A5-B1-C19; | A6-B1-C24; | A7-B1-C29; |
| A2-B1-C5; | A3-B1-C10; | A4-B1-C15; | A5-B1-C20; | A6-B1-C25; | A7-B1-C30; |
| A2-B1-C6; | A3-B1-C11; | A4-B1-C16; | A5-B1-C21; | A6-B1-C26; | A8-B1-C1; |
| A2-B1-C7; | A3-B1-C12; | A4-B1-C17; | A5-B1-C22; | A6-B1-C27; | A8-B1-C2; |
| A2-B1-C8; | A3-B1-C13; | A4-B1-C18; | A5-B1-C23; | A6-B1-C28; | A8-B1-C3; |
| A2-B1-C9; | A3-B1-C14; | A4-B1-C19; | A5-B1-C24; | A6-B1-C29; | A8-B1-C4; |
| A2-B1-C10; | A3-B1-C15; | A4-B1-C20; | A5-B1-C25; | A6-B1-C30; | A8-B1-C5; |
| A2-B1-C11; | A3-B1-C16; | A4-B1-C21; | A5-B1-C26; | A7-B1-C1; | A8-B1-C6; |
| A2-B1-C12; | A3-B1-C17; | A4-B1-C22; | A5-B1-C27; | A7-B1-C2; | A8-B1-C7; |
| A2-B1-C13; | A3-B1-C18; | A4-B1-C23; | A5-B1-C28; | A7-B1-C3; | A8-B1-C8; |
| A2-B1-C14; | A3-B1-C19; | A4-B1-C24; | A5-B1-C29; | A7-B1-C4; | A8-B1-C9; |
| A2-B1-C15; | A3-B1-C20; | A4-B1-C25; | A5-B1-C30; | A7-B1-C5; | A8-B1-C10; |
| A2-B1-C16; | A3-B1-C21; | A4-B1-C26; | A6-B1-C1; | A7-B1-C6; | A8-B1-C11; |
| A2-B1-C17; | A3-B1-C22; | A4-B1-C27; | A6-B1-C2; | A7-B1-C7; | A8-B1-C12; |
| A2-B1-C18; | A3-B1-C23; | A4-B1-C28; | A6-B1-C3; | A7-B1-C8; | A8-B1-C13; |
| A2-B1-C19; | A3-B1-C24; | A4-B1-C29; | A6-B1-C4; | A7-B1-C9; | A8-B1-C14; |
| A2-B1-C20; | A3-B1-C25; | A4-B1-C30; | A6-B1-C5; | A7-B1-C10; | A8-B1-C15; |
| A2-B1-C21; | A3-B1-C26; | A5-B1-C1; | A6-B1-C6; | A7-B1-C11; | A8-B1-C16; |
| A2-B1-C22; | A3-B1-C27; | A5-B1-C2; | A6-B1-C7; | A7-B1-C12; | A8-B1-C17; |
| A2-B1-C23; | A3-B1-C28; | A5-B1-C3; | A6-B1-C8; | A7-B1-C13; | A8-B1-C18; |
| A2-B1-C24; | A3-B1-C29; | A5-B1-C4; | A6-B1-C9; | A7-B1-C14; | A8-B1-C19; |
| A2-B1-C25; | A3-B1-C30; | A5-B1-C5; | A6-B1-C10; | A7-B1-C15; | A8-B1-C20; |
| A2-B1-C26; | A4-B1-C1; | A5-B1-C6; | A6-B1-C11; | A7-B1-C16; | A8-B1-C21; |
| A2-B1-C27; | A4-B1-C2; | A5-B1-C7; | A6-B1-C12; | A7-B1-C17; | A8-B1-C22; |
| A2-B1-C28; | A4-B1-C3; | A5-B1-C8; | A6-B1-C13; | A7-B1-C18; | A8-B1-C23; |
| A2-B1-C29; | A4-B1-C4; | A5-B1-C9; | A6-B1-C14; | A7-B1-C19; | A8-B1-C24; |
| A2-B1-C30; | A4-B1-C5; | A5-B1-C10; | A6-B1-C15; | A7-B1-C20; | A8-B1-C25; |
| A3-B1-C1; | A4-B1-C6; | A5-B1-C11; | A6-B1-C16; | A7-B1-C21; | A8-B1-C26; |
| A3-B1-C2; | A4-B1-C7; | A5-B1-C12; | A6-B1-C17; | A7-B1-C22; | A8-B1-C27; |
| A3-B1-C3; | A4-B1-C8; | A5-B1-C13; | A6-B1-C18; | A7-B1-C23; | A8-B1-C28; |
| A3-B1-C4; | A4-B1-C9; | A5-B1-C14; | A6-B1-C19; | A7-B1-C24; | A8-B1-C29; |
| A3-B1-C5; | A4-B1-C10; | A5-B1-C15; | A6-B1-C20; | A7-B1-C25; | A8-B1-C30; |
| A9-B1-C1; | A10-B1-C6; | A11-B1-C11; | A12-B1-C16; | A13-B1-C21; | A14-B1-C26; |
| A9-B1-C2; | A10-B1-C7; | A11-B1-C12; | A12-B1-C17; | A13-B1-C22; | A14-B1-C27; |
| A9-B1-C3; | A10-B1-C8; | A11-B1-C13; | A12-B1-C18; | A13-B1-C23; | A14-B1-C28; |
| A9-B1-C4; | A10-B1-C9; | A11-B1-C14; | A12-B1-C19; | A13-B1-C24; | A14-B1-C29; |
| A9-B1-C5; | A10-B1-C10; | A11-B1-C15; | A12-B1-C20; | A13-B1-C25; | A14-B1-C30; |
| A9-B1-C6; | A10-B1-C11; | A11-B1-C16; | A12-B1-C21; | A13-B1-C26; | A15-B1-C1; |
| A9-B1-C7; | A10-B1-C12; | A11-B1-C17; | A12-B1-C22; | A13-B1-C27; | A15-B1-C2; |
| A9-B1-C8; | A10-B1-C13; | A11-B1-C18; | A12-B1-C23; | A13-B1-C28; | A15-B1-C3; |
| A9-B1-C9; | A10-B1-C14; | A11-B1-C19; | A12-B1-C24; | A13-B1-C29; | A15-B1-C4; |
| A9-B1-C10; | A10-B1-C15; | A11-B1-C20; | A12-B1-C25; | A13-B1-C30; | A15-B1-C5; |
| A9-B1-C11; | A10-B1-C16; | A11-B1-C21; | A12-B1-C26; | A14-B1-C1; | A15-B1-C6; |
| A9-B1-C12; | A10-B1-C17; | A11-B1-C22; | A12-B1-C27; | A14-B1-C2; | A15-B1-C7; |
| A9-B1-C13; | A10-B1-C18; | A11-B1-C23; | A12-B1-C28; | A14-B1-C3; | A15-B1-C8; |
| A9-B1-C14; | A10-B1-C19; | A11-B1-C24; | A12-B1-C29; | A14-B1-C4; | A15-B1-C9; |
| A9-B1-C15; | A10-B1-C20; | A11-B1-C25; | A12-B1-C30; | A14-B1-C5; | A15-B1-C10; |
| A9-B1-C16; | A10-B1-C21; | A11-B1-C26; | A13-B1-C1; | A14-B1-C6; | A15-B1-C11; |
| A9-B1-C17; | A10-B1-C22; | A11-B1-C27; | A13-B1-C2; | A14-B1-C7; | A15-B1-C12; |
| A9-B1-C18; | A10-B1-C23; | A11-B1-C28; | A13-B1-C3; | A14-B1-C8; | A15-B1-C13; |
| A9-B1-C19; | A10-B1-C24; | A11-B1-C29; | A13-B1-C4; | A14-B1-C9; | A15-B1-C14; |
| A9-B1-C20; | A10-B1-C25; | A11-B1-C30; | A13-B1-C5; | A14-B1-C10; | A15-B1-C15; |
| A9-B1-C21; | A10-B1-C26; | A12-B1-C1; | A13-B1-C6; | A14-B1-C11; | A15-B1-C16; |
| A9-B1-C22; | A10-B1-C27; | A12-B1-C2; | A13-B1-C7; | A14-B1-C12; | A15-B1-C17; |
| A9-B1-C23; | A10-B1-C28; | A12-B1-C3; | A13-B1-C8; | A14-B1-C13; | A15-B1-C18; |
| A9-B1-C24; | A10-B1-C29; | A12-B1-C4; | A13-B1-C9; | A14-B1-C14; | A15-B1-C19; |
| A9-B1-C25; | A10-B1-C30; | A12-B1-C5; | A13-B1-C10; | A14-B1-C15; | A15-B1-C20; |
| A9-B1-C26; | A11-B1-C1; | A12-B1-C6; | A13-B1-C11; | A14-B1-C16; | A15-B1-C21; |
| A9-B1-C27; | A11-B1-C2; | A12-B1-C7; | A13-B1-C12; | A14-B1-C17; | A15-B1-C22; |
| A9-B1-C28; | A11-B1-C3; | A12-B1-C8; | A13-B1-C13; | A14-B1-C18; | A15-B1-C23; |
| A9-B1-C29; | A11-B1-C4; | A12-B1-C9; | A13-B1-C14; | A14-B1-C19; | A15-B1-C24; |
| A9-B1-C30; | A11-B1-C5; | A12-B1-C10; | A13-B1-C15; | A14-B1-C20; | A15-B1-C25; |
| A10-B1-C1; | A11-B1-C6; | A12-B1-C11; | A13-B1-C16; | A14-B1-C21; | A15-B1-C26; |
| A10-B1-C2; | A11-B1-C7; | A12-B1-C12; | A13-B1-C17; | A14-B1-C22; | A15-B1-C27; |
| A10-B1-C3; | A11-B1-C8; | A12-B1-C13; | A13-B1-C18; | A14-B1-C23; | A15-B1-C28; |
| A10-B1-C4; | A11-B1-C9; | A12-B1-C14; | A13-B1-C19; | A14-B1-C24; | A15-B1-C29; |
| A10-B1-C5; | A11-B1-C10; | A12-B1-C15; | A13-B1-C20; | A14-B1-C25; | A15-B1-C30; |
| A16-B1-C1; | A17-B1-C6; | A18-B1-C11; | A19-B1-C16; | A20-B1-C21; | A21-B1-C26; |
| A16-B1-C2; | A17-B1-C7; | A18-B1-C12; | A19-B1-C17; | A20-B1-C22; | A21-B1-C27; |
| A16-B1-C3; | A17-B1-C8; | A18-B1-C13; | A19-B1-C18; | A20-B1-C23; | A21-B1-C28; |
| A16-B1-C4; | A17-B1-C9; | A18-B1-C14; | A19-B1-C19; | A20-B1-C24; | A21-B1-C29; |

-continued

| | | | | | |
|---|---|---|---|---|---|
| A16-B1-C5; | A17-B1-C10; | A18-B1-C15; | A19-B1-C20; | A20-B1-C25; | A21-B1-C30; |
| A16-B1-C6; | A17-B1-C11; | A18-B1-C16; | A19-B1-C21; | A20-B1-C26; | A22-B1-C1; |
| A16-B1-C7; | A17-B1-C12; | A18-B1-C17; | A19-B1-C22; | A20-B1-C27; | A22-B1-C2; |
| A16-B1-C8; | A17-B1-C13; | A18-B1-C18; | A19-B1-C23; | A20-B1-C28; | A22-B1-C3; |
| A16-B1-C9; | A17-B1-C14; | A18-B1-C19; | A19-B1-C24; | A20-B1-C29; | A22-B1-C4; |
| A16-B1-C10; | A17-B1-C15; | A18-B1-C20; | A19-B1-C25; | A20-B1-C30; | A22-B1-C5; |
| A16-B1-C11; | A17-B1-C16; | A18-B1-C21; | A19-B1-C26; | A21-B1-C1; | A22-B1-C6; |
| A16-B1-C12; | A17-B1-C17; | A18-B1-C22; | A19-B1-C27; | A21-B1-C2; | A22-B1-C7; |
| A16-B1-C13; | A17-B1-C18; | A18-B1-C23; | A19-B1-C28; | A21-B1-C3; | A22-B1-C8; |
| A16-B1-C14; | A17-B1-C19; | A18-B1-C24; | A19-B1-C29; | A21-B1-C4; | A22-B1-C9; |
| A16-B1-C15; | A17-B1-C20; | A18-B1-C25; | A19-B1-C30; | A21-B1-C5; | A22-B1-C10; |
| A16-B1-C16; | A17-B1-C21; | A18-B1-C26; | A20-B1-C1; | A21-B1-C6; | A22-B1-C11; |
| A16-B1-C17; | A17-B1-C22; | A18-B1-C27; | A20-B1-C2; | A21-B1-C7; | A22-B1-C12; |
| A16-B1-C18; | A17-B1-C23; | A18-B1-C28; | A20-B1-C3; | A21-B1-C8; | A22-B1-C13; |
| A16-B1-C19; | A17-B1-C24; | A18-B1-C29; | A20-B1-C4; | A21-B1-C9; | A22-B1-C14; |
| A16-B1-C20; | A17-B1-C25; | A18-B1-C30; | A20-B1-C5; | A21-B1-C10; | A22-B1-C15; |
| A16-B1-C21; | A17-B1-C26; | A19-B1-C1; | A20-B1-C6; | A21-B1-C11; | A22-B1-C16; |
| A16-B1-C22; | A17-B1-C27; | A19-B1-C2; | A20-B1-C7; | A21-B1-C12; | A22-B1-C17; |
| A16-B1-C23; | A17-B1-C28; | A19-B1-C3; | A20-B1-C8; | A21-B1-C13; | A22-B1-C18; |
| A16-B1-C24; | A17-B1-C29; | A19-B1-C4; | A20-B1-C9; | A21-B1-C14; | A22-B1-C19; |
| A16-B1-C25; | A17-B1-C30; | A19-B1-C5; | A20-B1-C10; | A21-B1-C15; | A22-B1-C20; |
| A16-B1-C26; | A18-B1-C1; | A19-B1-C6; | A20-B1-C11; | A21-B1-C16; | A22-B1-C21; |
| A16-B1-C27; | A18-B1-C2; | A19-B1-C7; | A20-B1-C12; | A21-B1-C17; | A22-B1-C22; |
| A16-B1-C28; | A18-B1-C3; | A19-B1-C8; | A20-B1-C13; | A21-B1-C18; | A22-B1-C23; |
| A16-B1-C29; | A18-B1-C4; | A19-B1-C9; | A20-B1-C14; | A21-B1-C19; | A22-B1-C24; |
| A16-B1-C30; | A18-B1-C5; | A19-B1-C10; | A20-B1-C15; | A21-B1-C20; | A22-B1-C25; |
| A17-B1-C1; | A18-B1-C6; | A19-B1-C11; | A20-B1-C16; | A21-B1-C21; | A22-B1-C26; |
| A17-B1-C2; | A18-B1-C7; | A19-B1-C12; | A20-B1-C17; | A21-B1-C22; | A22-B1-C27; |
| A17-B1-C3; | A18-B1-C8; | A19-B1-C13; | A20-B1-C18; | A21-B1-C23; | A22-B1-C28; |
| A17-B1-C4; | A18-B1-C9; | A19-B1-C14; | A20-B1-C19; | A21-B1-C24; | A22-B1-C29; |
| A17-B1-C5; | A18-B1-C10; | A19-B1-C15; | A20-B1-C20; | A21-B1-C25; | A22-B1-C30; |
| A23-B1-C1; | A24-B1-C6; | A25-B1-C11; | A26-B1-C16; | A27-B1-C21; | A28-B1-C26; |
| A23-B1-C2; | A24-B1-C7; | A25-B1-C12; | A26-B1-C17; | A27-B1-C22; | A28-B1-C27; |
| A23-B1-C3; | A24-B1-C8; | A25-B1-C13; | A26-B1-C18; | A27-B1-C23; | A28-B1-C28; |
| A23-B1-C4; | A24-B1-C9; | A25-B1-C14; | A26-B1-C19; | A27-B1-C24; | A28-B1-C29; |
| A23-B1-C5; | A24-B1-C10; | A25-B1-C15; | A26-B1-C20; | A27-B1-C25; | A28-B1-C30; |
| A23-B1-C6; | A24-B1-C11; | A25-B1-C16; | A26-B1-C21; | A27-B1-C26; | A29-B1-C1; |
| A23-B1-C7; | A24-B1-C12; | A25-B1-C17; | A26-B1-C22; | A27-B1-C27; | A29-B1-C2; |
| A23-B1-C8; | A24-B1-C13; | A25-B1-C18; | A26-B1-C23; | A27-B1-C28; | A29-B1-C3; |
| A23-B1-C9; | A24-B1-C14; | A25-B1-C19; | A26-B1-C24; | A27-B1-C29; | A29-B1-C4; |
| A23-B1-C10; | A24-B1-C15; | A25-B1-C20; | A26-B1-C25; | A27-B1-C30; | A29-B1-C5; |
| A23-B1-C11; | A24-B1-C16; | A25-B1-C21; | A26-B1-C26; | A28-B1-C1; | A29-B1-C6; |
| A23-B1-C12; | A24-B1-C17; | A25-B1-C22; | A26-B1-C27; | A28-B1-C2; | A29-B1-C7; |
| A23-B1-C13; | A24-B1-C18; | A25-B1-C23; | A26-B1-C28; | A28-B1-C3; | A29-B1-C8; |
| A23-B1-C14; | A24-B1-C19; | A25-B1-C24; | A26-B1-C29; | A28-B1-C4; | A29-B1-C9; |
| A23-B1-C15; | A24-B1-C20; | A25-B1-C25; | A26-B1-C30; | A28-B1-C5; | A29-B1-C10; |
| A23-B1-C16; | A24-B1-C21; | A25-B1-C26; | A27-B1-C1; | A28-B1-C6; | A29-B1-C11; |
| A23-B1-C17; | A24-B1-C22; | A25-B1-C27; | A27-B1-C2; | A28-B1-C7; | A29-B1-C12; |
| A23-B1-C18; | A24-B1-C23; | A25-B1-C28; | A27-B1-C3; | A28-B1-C8; | A29-B1-C13; |
| A23-B1-C19; | A24-B1-C24; | A25-B1-C29; | A27-B1-C4; | A28-B1-C9; | A29-B1-C14; |
| A23-B1-C20; | A24-B1-C25; | A25-B1-C30; | A27-B1-C5; | A28-B1-C10; | A29-B1-C15; |
| A23-B1-C21; | A24-B1-C26; | A26-B1-C1; | A27-B1-C6; | A28-B1-C11; | A29-B1-C16; |
| A23-B1-C22; | A24-B1-C27; | A26-B1-C2; | A27-B1-C7; | A28-B1-C12; | A29-B1-C17; |
| A23-B1-C23; | A24-B1-C28; | A26-B1-C3; | A27-B1-C8; | A28-B1-C13; | A29-B1-C18; |
| A23-B1-C24; | A24-B1-C29; | A26-B1-C4; | A27-B1-C9; | A28-B1-C14; | A29-B1-C19; |
| A23-B1-C25; | A24-B1-C30; | A26-B1-C5; | A27-B1-C10; | A28-B1-C15; | A29-B1-C20; |
| A23-B1-C26; | A25-B1-C1; | A26-B1-C6; | A27-B1-C11; | A28-B1-C16; | A29-B1-C21; |
| A23-B1-C27; | A25-B1-C2; | A26-B1-C7; | A27-B1-C12; | A28-B1-C17; | A29-B1-C22; |
| A23-B1-C28; | A25-B1-C3; | A26-B1-C8; | A27-B1-C13; | A28-B1-C18; | A29-B1-C23; |
| A23-B1-C29; | A25-B1-C4; | A26-B1-C9; | A27-B1-C14; | A28-B1-C19; | A29-B1-C24; |
| A23-B1-C30; | A25-B1-C5; | A26-B1-C10; | A27-B1-C15; | A28-B1-C20; | A29-B1-C25; |
| A24-B1-C1; | A25-B1-C6; | A26-B1-C11; | A27-B1-C16; | A28-B1-C21; | A29-B1-C26; |
| A24-B1-C2; | A25-B1-C7; | A26-B1-C12; | A27-B1-C17; | A28-B1-C22; | A29-B1-C27; |
| A24-B1-C3; | A25-B1-C8; | A26-B1-C13; | A27-B1-C18; | A28-B1-C23; | A29-B1-C28; |
| A24-B1-C4; | A25-B1-C9; | A26-B1-C14; | A27-B1-C19; | A28-B1-C24; | A29-B1-C29; |
| A24-B1-C5; | A25-B1-C10; | A26-B1-C15; | A27-B1-C20; | A28-B1-C25; | A29-B1-C30; |
| A30-B1-C1; | A31-B1-C6; | A32-B1-C11; | A1-B2-C16; | A2-B2-C21; | A3-B2-C26; |
| A30-B1-C2; | A31-B1-C7; | A32-B1-C12; | A1-B2-C17; | A2-B2-C22; | A3-B2-C27; |
| A30-B1-C3; | A31-B1-C8; | A32-B1-C13; | A1-B2-C18; | A2-B2-C23; | A3-B2-C28; |
| A30-B1-C4; | A31-B1-C9; | A32-B1-C14; | A1-B2-C19; | A2-B2-C24; | A3-B2-C29; |
| A30-B1-C5; | A31-B1-C10; | A32-B1-C15; | A1-B2-C20; | A2-B2-C25; | A3-B2-C30; |
| A30-B1-C6; | A31-B1-C11; | A32-B1-C16; | A1-B2-C21; | A2-B2-C26; | A4-B2-C1; |
| A30-B1-C7; | A31-B1-C12; | A32-B1-C17; | A1-B2-C22; | A2-B2-C27; | A4-B2-C2; |
| A30-B1-C8; | A31-B1-C13; | A32-B1-C18; | A1-B2-C23; | A2-B2-C28; | A4-B2-C3; |
| A30-B1-C9; | A31-B1-C14; | A32-B1-C19; | A1-B2-C24; | A2-B2-C29; | A4-B2-C4; |
| A30-B1-C10; | A31-B1-C15; | A32-B1-C20; | A1-B2-C25; | A2-B2-C30; | A4-B2-C5; |
| A30-B1-C11; | A31-B1-C16; | A32-B1-C21; | A1-B2-C26; | A3-B2-C1; | A4-B2-C6; |
| A30-B1-C12; | A31-B1-C17; | A32-B1-C22; | A1-B2-C27; | A3-B2-C2; | A4-B2-C7; |
| A30-B1-C13; | A31-B1-C18; | A32-B1-C23; | A1-B2-C28; | A3-B2-C3; | A4-B2-C8; |

-continued

| | | | | | |
|---|---|---|---|---|---|
| A30-B1-C14; | A31-B1-C19; | A32-B1-C24; | A1-B2-C29; | A3-B2-C4; | A4-B2-C9; |
| A30-B1-C15; | A31-B1-C20; | A32-B1-C25; | A1-B2-C30; | A3-B2-C5; | A4-B2-C10; |
| A30-B1-C16; | A31-B1-C21; | A32-B1-C26; | A2-B2-C1; | A3-B2-C6; | A4-B2-C11; |
| A30-B1-C17; | A31-B1-C22; | A32-B1-C27; | A2-B2-C2; | A3-B2-C7; | A4-B2-C12; |
| A30-B1-C18; | A31-B1-C23; | A32-B1-C28; | A2-B2-C3; | A3-B2-C8; | A4-B2-C13; |
| A30-B1-C19; | A31-B1-C24; | A32-B1-C29; | A2-B2-C4; | A3-B2-C9; | A4-B2-C14; |
| A30-B1-C20; | A31-B1-C25; | A32-B1-C30; | A2-B2-C5; | A3-B2-C10; | A4-B2-C15; |
| A30-B1-C21; | A31-B1-C26; | A1-B2-C1; | A2-B2-C6; | A3-B2-C11; | A4-B2-C16; |
| A30-B1-C22; | A31-B1-C27; | A1-B2-C2; | A2-B2-C7; | A3-B2-C12; | A4-B2-C17; |
| A30-B1-C23; | A31-B1-C28; | A1-B2-C3; | A2-B2-C8; | A3-B2-C13; | A4-B2-C18; |
| A30-B1-C24; | A31-B1-C29; | A1-B2-C4; | A2-B2-C9; | A3-B2-C14; | A4-B2-C19; |
| A30-B1-C25; | A31-B1-C30; | A1-B2-C5; | A2-B2-C10; | A3-B2-C15; | A4-B2-C20; |
| A30-B1-C26; | A32-B1-C1; | A1-B2-C6; | A2-B2-C11; | A3-B2-C16; | A4-B2-C21; |
| A30-B1-C27; | A32-B1-C2; | A1-B2-C7; | A2-B2-C12; | A3-B2-C17; | A4-B2-C22; |
| A30-B1-C28; | A32-B1-C3; | A1-B2-C8; | A2-B2-C13; | A3-B2-C18; | A4-B2-C23; |
| A30-B1-C29; | A32-B1-C4; | A1-B2-C9; | A2-B2-C14; | A3-B2-C19; | A4-B2-C24; |
| A30-B1-C30; | A32-B1-C5; | A1-B2-C10; | A2-B2-C15; | A3-B2-C20; | A4-B2-C25; |
| A31-B1-C1; | A32-B1-C6; | A1-B2-C11; | A2-B2-C16; | A3-B2-C21; | A4-B2-C26; |
| A31-B1-C2; | A32-B1-C7; | A1-B2-C12; | A2-B2-C17; | A3-B2-C22; | A4-B2-C27; |
| A31-B1-C3; | A32-B1-C8; | A1-B2-C13; | A2-B2-C18; | A3-B2-C23; | A4-B2-C28; |
| A31-B1-C4; | A32-B1-C9; | A1-B2-C14; | A2-B2-C19; | A3-B2-C24; | A4-B2-C29; |
| A31-B1-C5; | A32-B1-C10; | A1-B2-C15; | A2-B2-C20; | A3-B2-C25; | A4-B2-C30; |
| A5-B2-C1; | A6-B2-C6; | A7-B2-C11; | A8-B2-C16; | A9-B2-C21; | A10-B2-C26; |
| A5-B2-C2; | A6-B2-C7; | A7-B2-C12; | A8-B2-C17; | A9-B2-C22; | A10-B2-C27; |
| A5-B2-C3; | A6-B2-C8; | A7-B2-C13; | A8-B2-C18; | A9-B2-C23; | A10-B2-C28; |
| A5-B2-C4; | A6-B2-C9; | A7-B2-C14; | A8-B2-C19; | A9-B2-C24; | A10-B2-C29; |
| A5-B2-C5; | A6-B2-C10; | A7-B2-C15; | A8-B2-C20; | A9-B2-C25; | A10-B2-C30; |
| A5-B2-C6; | A6-B2-C11; | A7-B2-C16; | A8-B2-C21; | A9-B2-C26; | A11-B2-C1; |
| A5-B2-C7; | A6-B2-C12; | A7-B2-C17; | A8-B2-C22; | A9-B2-C27; | A11-B2-C2; |
| A5-B2-C8; | A6-B2-C13; | A7-B2-C18; | A8-B2-C23; | A9-B2-C28; | A11-B2-C3; |
| A5-B2-C9; | A6-B2-C14; | A7-B2-C19; | A8-B2-C24; | A9-B2-C29; | A11-B2-C4; |
| A5-B2-C10; | A6-B2-C15; | A7-B2-C20; | A8-B2-C25; | A9-B2-C30; | A11-B2-C5; |
| A5-B2-C11; | A6-B2-C16; | A7-B2-C21; | A8-B2-C26; | A10-B2-C1; | A11-B2-C6; |
| A5-B2-C12; | A6-B2-C17; | A7-B2-C22; | A8-B2-C27; | A10-B2-C2; | A11-B2-C7; |
| A5-B2-C13; | A6-B2-C18; | A7-B2-C23; | A8-B2-C28; | A10-B2-C3; | A11-B2-C8; |
| A5-B2-C14; | A6-B2-C19; | A7-B2-C24; | A8-B2-C29; | A10-.B2-C4; | A11-B2-C9; |
| A5-B2-C15; | A6-B2-C20; | A7-B2-C25; | A8-B2-C30; | A10-B2-C5; | A11-B2-C10; |
| A5-B2-C16; | A6-B2-C21; | A7-B2-C26; | A9-B2-C1; | A10-B2-C6; | A11-B2-C11; |
| A5-B2-C17; | A6-B2-C22; | A7-B2-C27; | A9-B2-C2; | A10-B2-C7; | A11-B2-C12; |
| A5-B2-C18; | A6-B2-C23; | A7-B2-C28; | A9-B2-C3; | A10-B2-C8; | A11-B2-C13; |
| A5-B2-C19; | A6-B2-C24; | A7-B2-C29; | A9-B2-C4; | A10-B2-C9; | A11-B2-C14; |
| A5-B2-C20; | A6-B2-C25; | A7-B2-C30; | A9-B2-C5; | A10-B2-C10; | A11-B2-C15; |
| A5-B2-C21; | A6-B2-C26; | A8-B2-C1; | A9-B2-C6; | A10-B2-C11; | A11-B2-C16; |
| A5-B2-C22; | A6-B2-C27; | A8-B2-C2; | A9-B2-C7; | A10-B2-C12; | A11-B2-C17; |
| A5-B2-C23; | A6-B2-C28; | A8-B2-C3; | A9-B2-C8; | A10-B2-C13; | A11-B2-C18; |
| A5-B2-C24; | A6-B2-C29; | A8-B2-C4; | A9-B2-C9; | A10-B2-C14; | A11-B2-C19; |
| A5-B2-C25; | A6-B2-C30; | A8-B2-C5; | A9-B2-C10; | A10-B2-C15; | A11-B2-C20; |
| A5-B2-C26; | A7-B2-C1; | A8-B2-C6; | A9-B2-C11; | A10-B2-C16; | A11-B2-C21; |
| A5-B2-C27; | A7-B2-C2; | A8-B2-C7; | A9-B2-C12; | A10-B2-C17; | A11-B2-C22; |
| A5-B2-C28; | A7-B2-C3; | A8-B2-C8; | A9-B2-C13; | A10-B2-C18; | A11-B2-C23; |
| A5-B2-C29; | A7-B2-C4; | A8-B2-C9; | A9-B2-C14; | A10-B2-C19; | A11-B2-C24; |
| A5-B2-C30; | A7-B2-C5; | A8-B2-C10; | A9-B2-C15; | A10-B2-C20; | A11-B2-C25; |
| A6-B2-C1; | A7-B2-C6; | A8-B2-C11; | A9-B2-C16; | A10-B2-C21; | A11-B2-C26; |
| A6-B2-C2; | A7-B2-C7; | A8-B2-C12; | A9-B2-C17; | A10-B2-C22; | A11-B2-C27; |
| A6-B2-C3; | A7-B2-C8; | A8-B2-C13; | A9-B2-C18; | A10-B2-C23; | A11-B2-C28; |
| A6-B2-C4; | A7-B2-C9; | A8-B2-C14; | A9-B2-C19; | A10-B2-C24; | A11-B2-C29; |
| A6-B2-C5; | A7-B2-C10; | A8-B2-C15; | A9-B2-C20; | A10-B2-C25; | A11-B2-C30; |
| A12-B2-C1; | A13-B2-C6; | A14-B2-C11; | A15-B2-C16; | A16-B2-C21; | A17-B2-C26; |
| A12-B2-C2; | A13-B2-C7; | A14-B2-C12; | A15-B2-C17; | A16-B2-C22; | A17-B2-C27; |
| A12-B2-C3; | A13-B2-C8; | A14-B2-C13; | A15-B2-C18; | A16-B2-C23; | A17-B2-C28; |
| A12-B2-C4; | A13-B2-C9; | A14-B2-C14; | A15-B2-C19; | A16-B2-C24; | A17-B2-C29; |
| A12-B2-C5; | A13-B2-C10; | A14-B2-C15; | A15-B2-C20; | A16-B2-C25; | A17-B2-C30; |
| A12-B2-C6; | A13-B2-C11; | A14-B2-C16; | A15-B2-C21; | A16-B2-C26; | A18-B2-C1; |
| A12-B2-C7; | A13-B2-C12; | A14-B2-C17; | A15-B2-C22; | A16-B2-C27; | A18-B2-C2; |
| A12-B2-C8; | A13-B2-C13; | A14-B2-C18; | A15-B2-C23; | A16-B2-C28; | A18-B2-C3; |
| A12-B2-C9; | A13-B2-C14; | A14-B2-C19; | A15-B2-C24; | A16-B2-C29; | A18-B2-C4; |
| A12-B2-C10; | A13-B2-C15; | A14-B2-C20; | A15-B2-C25; | A16-B2-C30; | A18-B2-C5; |
| A12-B2-C11; | A13-B2-C16; | A14-B2-C21; | A15-B2-C26; | A17-B2-C1; | A18-B2-C6; |
| A12-B2-C12; | A13-B2-C17; | A14-B2-C22; | A15-B2-C27; | A17-B2-C2; | A18-B2-C7; |
| A12-B2-C13; | A13-B2-C18; | A14-B2-C23; | A15-B2-C28; | A17-B2-C3; | A18-B2-C8; |
| A12-B2-C14; | A13-B2-C19; | A14-B2-C24; | A15-B2-C29; | A17-B2-C4; | A18-B2-C9; |
| A12-B2-C15; | A13-B2-C20; | A14-B2-C25; | A15-B2-C30; | A17-B2-C5; | A18-B2-C10; |
| A12-B2-C16; | A13-B2-C21; | A14-B2-C26; | A16-B2-C1; | A17-B2-C6; | A18-B2-C11; |
| A12-B2-C17; | A13-B2-C22; | A14-B2-C27; | A16-B2-C2; | A17-B2-C7; | A18-B2-C12; |
| A12-B2-C18; | A13-B2-C23; | A14-B2-C28; | A16-B2-C3; | A17-B2-C8; | A18-B2-C13; |
| A12-B2-C19; | A13-B2-C24; | A14-B2-C29; | A16-B2-C4; | A17-B2-C9; | A18-B2-C14; |
| A12-B2-C20; | A13-B2-C25; | A14-B2-C30; | A16-B2-C5; | A17-B2-C10; | A18-B2-C15; |
| A12-B2-C21; | A13-B2-C26; | A15-B2-C1; | A16-B2-C6; | A17-B2-C11; | A18-B2-C16; |
| A12-B2-C22; | A13-B2-C27; | A15-B2-C2; | A16-B2-C7; | A17-B2-C12; | A18-B2-C17; |

-continued

| | | | | | |
|---|---|---|---|---|---|
| A12-B2-C23; | A13-B2-C28; | A15-B2-C3; | A16-B2-C8; | A17-B2-C13; | A18-B2-C18; |
| A12-B2-C24; | A13-B2-C29; | A15-B2-C4; | A16-B2-C9; | A17-B2-C14; | A18-B2-C19; |
| A12-B2-C25; | A13-B2-C30; | A15-B2-C5; | A16-B2-C10; | A17-B2-C15; | A18-B2-C20; |
| A12-B2-C26; | A14-B2-C1; | A15-B2-C6; | A16-B2-C11; | A17-B2-C16; | A18-B2-C21; |
| A12-B2-C27; | A14-B2-C2; | A15-B2-C7; | A16-B2-C12; | A17-B2-C17; | A18-B2-C22; |
| A12-B2-C28; | A14-B2-C3; | A15-B2-C8; | A16-B2-C13; | A17-B2-C18; | A18-B2-C23; |
| A12-B2-C29; | A14-B2-C4; | A15-B2-C9; | A16-B2-C14; | A17-B2-C19; | A18-B2-C24; |
| A12-B2-C30; | A14-B2-C5; | A15-B2-C10; | A16-B2-C15; | A17-b2-C20; | A18-B2-C25; |
| A13-B2-C1; | A14-B2-C6; | A15-B2-C11; | A16-B2-C16; | A17-B2-C21; | A18-B2-C26; |
| A13-B2-C2; | A14-B2-C7; | A15-B2-C12; | A16-B2-C17; | A17-B2-C22; | A18-B2-C27; |
| A13-B2-C3; | A14-B2-C8; | A15-B2-C13; | A16-B2-C18; | A17-B2-C23; | A18-B2-C28; |
| A13-B2-C4; | A14-B2-C9; | A15-B2-C14; | A16-B2-C19; | A17-B2-C24; | A18-B2-C29; |
| A13-B2-C5; | A14-B2-C10; | A15-B2-C15; | A16-B2-C20; | A17-B2-C25; | A18-B2-C30; |
| A19-B2-C1; | A20-B2-C6; | A21-B2-C11; | A22-B2-C16; | A23-B2-C21; | A24-B2-C26; |
| A19-B2-C2; | A20-B2-C7; | A21-B2-C12; | A22-B2-C17; | A23-B2-C22; | A24-B2-C27; |
| A19-B2-C3; | A20-B2-C8; | A21-B2-C13; | A22-B2-C18; | A23-B2-C23; | A24-B2-C28; |
| A19-B2-C4; | A20-B2-C9; | A21-B2-C14; | A22-B2-C19; | A23-B2-C24; | A24-B2-C29; |
| A19-B2-C5; | A20-B2-C10; | A21-B2-C15; | A22-B2-C20; | A23-B2-C25; | A24-B2-C30; |
| A19-B2-C6; | A20-B2-C11; | A21-B2-C16; | A22-B2-C21; | A23-B2-C26; | A25-B2-C1; |
| A19-B2-C7; | A20-B2-C12; | A21-B2-C17; | A22-B2-C22; | A23-B2-C27; | A25-B2-C2; |
| A19-B2-C8; | A20-B2-C13; | A21-B2-C18; | A22-B2-C23; | A23-B2-C28; | A25-B2-C3; |
| A19-B2-C9; | A20-B2-C14; | A21-B2-C19; | A22-B2-C24; | A23-B2-C29; | A25-B2-C4; |
| A19-B2-C10; | A20-B2-C15; | A21-B2-C20; | A22-B2-C25; | A23-B2-C30; | A25-B2-C5; |
| A19-B2-C11; | A20-B2-C16; | A21-B2-C21; | A22-B2-C26; | A24-B2-C1; | A25-B2-C6; |
| A19-B2-C12; | A20-B2-C17; | A21-B2-C22; | A22-B2-C27; | A24-B2-C2; | A25-B2-C7; |
| A19-B2-C13; | A20-B2-C18; | A21-B2-C23; | A22-B2-C28; | A24-B2-C3; | A25-B2-C8; |
| A19-B2-C14; | A20-B2-C19; | A21-B2-C24; | A22-B2-C29; | A24-B2-C4; | A25-B2-C9; |
| A19-B2-C15; | A20-B2-C20; | A21-B2-C25; | A22-B2-C30; | A24-B2-C5; | A25-B2-C10; |
| A19-B2-C16; | A20-B2-C21; | A21-B2-C26; | A23-B2-C1; | A24-B2-C6; | A25-B2-C11; |
| A19-B2-C17; | A20-B2-C22; | A21-B2-C27; | A23-B2-C2; | A24-B2-C7; | A25-B2-C12; |
| A19-B2-C18; | A20-B2-C23; | A21-B2-C28; | A23-B2-C3; | A24-B2-C8; | A25-B2-C13; |
| A19-B2-C19; | A20-B2-C24; | A21-B2-C29; | A23-B2-C4; | A24-B2-C9; | A25-B2-C14; |
| A19-B2-C20; | A20-B2-C25; | A21-B2-C30; | A23-B2-C5; | A24-B2-C10; | A25-B2-C15; |
| A19-B2-C21; | A20-B2-C26; | A22-B2-C1; | A23-B2-C6; | A24-B2-C11; | A25-B2-C16; |
| A19-B2-C22; | A20-B2-C27; | A22-B2-C2; | A23-B2-C7; | A24-B2-C12; | A25-B2-C17; |
| A19-B2-C23; | A20-B2-C28; | A22-B2-C3; | A23-B2-C8; | A24-B2-C13; | A25-B2-C18; |
| A19-B2-C24; | A20-B2-C29; | A22-B2-C4; | A23-B2-C9; | A24-B2-C14; | A25-B2-C19; |
| A19-B2-C25; | A20-B2-C30; | A22-B2-C5; | A23-B2-C10; | A24-B2-C15; | A25-B2-C20; |
| A19-B2-C26; | A21-B2-C1; | A22-B2-C6; | A23-B2-C11; | A24-B2-C16; | A25-B2-C21; |
| A19-B2-C27; | A21-B2-C2; | A22-B2-C7; | A23-B2-C12; | A24-B2-C17; | A25-B2-C22; |
| A19-B2-C28; | A21-B2-C3; | A22-B2-C8; | A23-B2-C13; | A24-B2-C18; | A25-B2-C23; |
| A19-B2-C29; | A21-B2-C4; | A22-B2-C9; | A23-B2-C14; | A24-B2-C19; | A25-B2-C24; |
| A19-B2-C30; | A21-B2-C5; | A22-B2-C10; | A23-B2-C15; | A24-B2-C20; | A25-B2-C25; |
| A20-B2-C1; | A21-B2-C6; | A22-B2-C11; | A23-B2-C16; | A24-B2-C21; | A25-B2-C26; |
| A20-B2-C2; | A21-B2-C7; | A22-B2-C12; | A23-B2-C17; | A24-B2-C22; | A25-B2-C27; |
| A20-B2-C3; | A21-B2-C8; | A22-B2-C13; | A23-B2-C18; | A24-B2-C23; | A25-B2-C28; |
| A20-B2-C4; | A21-B2-C9; | A22-B2-C14; | A23-B2-C19; | A24-B2-C24; | A25-B2-C29; |
| A20-B2-C5; | A21-B2-C10; | A22-B2-C15; | A23-B2-C20; | A24-B2-C25; | A25-B2-C30; |
| A26-B2-C1; | A27-B2-C6; | A28-B2-C11; | A29-B2-C16; | A30-B2-C21; | A31-B2-C26; |
| A26-B2-C2; | A27-B2-C7; | A28-B2-C12; | A29-B2-C17; | A30-B2-C22; | A31-B2-C27; |
| A26-B2-C3; | A27-B2-C8; | A28-B2-C13; | A29-B2-C18; | A30-B2-C23; | A31-B2-C28; |
| A26-B2-C4; | A27-B2-C9; | A28-B2-C14; | A29-B2-C19; | A30-B2-C24; | A31-B2-C29; |
| A26-B2-C5; | A27-B2-C10; | A28-B2-C15; | A29-B2-C20; | A30-B2-C25; | A31-B2-C30; |
| A26-B2-C6; | A27-B2-C11; | A28-B2-C16; | A29-B2-C21; | A30-B2-C26; | A32-B2-C1; |
| A26-B2-C7; | A27-B2-C12; | A28-B2-C17; | A29-B2-C22; | A30-B2-C27; | A32-B2-C2; |
| A26-B2-C8; | A27-B2-C13; | A28-B2-C18; | A29-B2-C23; | A30-B2-C28; | A32-B2-C3; |
| A26-B2-C9; | A27-B2-C14; | A28-B2-C19; | A29-B2-C24; | A30-B2-C29; | A32-B2-C4; |
| A26-B2-C10; | A27-B2-C15; | A28-B2-C20; | A29-B2-C25; | A30-B2-C30; | A32-B2-C5; |
| A26-B2-C11; | A27-B2-C16; | A28-B2-C21; | A29-B2-C26; | A31-B2-C1; | A32-B2-C6; |
| A26-B2-C12; | A27-B2-C17; | A28-B2-C22; | A29-B2-C27; | A31-B2-C2; | A32-B2-C7; |
| A26-B2-C13; | A27-B2-C18; | A28-B2-C23; | A29-B2-C28; | A31-B2-C3; | A32-B2-C8; |
| A26-B2-C14; | A27-B2-C19; | A28-B2-C24; | A29-B2-C29; | A31-B2-C4; | A32-B2-C9; |
| A26-B2-C15; | A27-B2-C20; | A28-B2-C25; | A29-B2-C30; | A31-B2-C5; | A32-B2-C10; |
| A26-B2-C16; | A27-B2-C21; | A28-B2-C26; | A30-B2-C1; | A31-B2-C6; | A32-B2-C11; |
| A26-B2-C17; | A27-B2-C22; | A28-B2-C27; | A30-B2-C2; | A31-B2-C7; | A32-B2-C12; |
| A26-B2-C18; | A27-B2-C23; | A28-B2-C28; | A30-B2-C3; | A31-B2-C8; | A32-B2-C13; |
| A26-B2-C19; | A27-B2-C24; | A28-B2-C29; | A30-B2-C4; | A31-B2-C9; | A32-B2-C14; |
| A26-B2-C20; | A27-B2-C25; | A28-B2-C30; | A30-B2-C5; | A31-B2-C10; | A32-B2-C15; |
| A26-B2-C21; | A27-B2-C26; | A29-B2-C1; | A30-B2-C6; | A31-B2-C11; | A32-B2-C16; |
| A26-B2-C22; | A27-B2-C27; | A29-B2-C2; | A30-B2-C7; | A31-B2-C12; | A32-B2-C17; |
| A26-B2-C23; | A27-B2-C28; | A29-B2-C3; | A30-B2-C8; | A31-B2-C13; | A32-B2-C18; |
| A26-B2-C24; | A27-B2-C29; | A29-B2-C4; | A30-B2-C9; | A31-B2-C14; | A32-B2-C19; |
| A26-B2-C25; | A27-B2-C30; | A29-B2-C5; | A30-B2-C10; | A31-B2-C15; | A32-B2-C20; |
| A26-B2-C26; | A28-B2-C1; | A29-B2-C6; | A30-B2-C11; | A31-B2-C16; | A32-B2-C21; |
| A26-B2-C27; | A28-B2-C2; | A29-B2-C7; | A30-B2-C12; | A31-B2-C17; | A32-B2-C22; |
| A26-B2-C28; | A28-B2-C3; | A29-B2-C8; | A30-B2-C13; | A31-B2-C18; | A32-B2-C23; |
| A26-B2-C29; | A28-B2-C4; | A29-B2-C9; | A30-B2-C14; | A31-B2-C19; | A32-B2-C24; |
| A26-B2-C30; | A28-B2-C5; | A29-B2-C10; | A30-B2-C15; | A31-B2-C20; | A32-B2-C25; |
| A27-B2-C1; | A28-B2-C6; | A29-B2-C11; | A30-B2-C16; | A31-B2-C21; | A32-B2-C26; |

| | | | | | |
|---|---|---|---|---|---|
| A27-B2-C2; | A28-B2-C7; | A29-B2-C12; | A30-B2-C17; | A31-B2-C22; | A32-B2-C27; |
| A27-B2-C3; | A28-B2-C8; | A29-B2-C13; | A30-B2-C18; | A31-B2-C23; | A32-B2-C28; |
| A27-B2-C4; | A28-B2-C9; | A29-B2-C14; | A30-B2-C19; | A31-B2-C24; | A32-B2-C29; |
| A27-B2-C5; | A28-B2-C10; | A29-B2-C15; | A30-B2-C20; | A31-B2-C25; | A32-B2-C30; | and the corresponding N-oxides, and their prodrugs; and pharmaceutically acceptable salts and solvates (e.g. hydrates) of such compounds and their N-oxides and prodrugs.

Thus, for example, in the above list the compound denoted as A1-B1-C2 is the product of the combination of group A1 in Table 1 and B1 in Table 2 and C2 in Table 3, namely

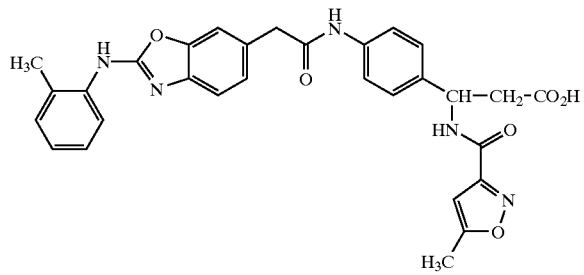

Preferred compounds of the invention are:
(R) 3-(benzoyl-amino)-3-(4-{[(2-o-tolylamino-benzoxazol-6-yl)-acetyl]-amino}-phenyl)-propionic acid;
(R) 3-[(5-methyl-isoxazole-3-carbonyl)-amino]-3-{4-[2-(2-o-tolylamino-benzoxazol-6-yl)-acetylamino]-phenyl}-propionic acid;
3-(4-{2-[2-(2-methoxy-phenylamino)-benzoxazol-6-yl]-acetylamino}-phenyl)-3-[(5-methylisoxazole-3-carbonyl)-amino]-propionic acid;
3-(4-{2-[2-(2-chloro-phenylamino)-benzoxazol-6-yl]-acetylamino}-phenyl)-3-[(5-methylisoxazole-3-carbonyl)-amino]-propionic acid;
3-(4-{2-[2-(2-chloro-phenylamino)-benzoxazol-6-yl]-acetylamino}-phenyl)-3-[(pyridine-4-carbonyl)-amino]-propionic acid;
3-(4-{2-[2-(2-methyl-phenylamino)-benzoxazol-6-yl]-acetylamino}-phenyl)-3-[(thiophene-2-carbonyl)-amino]-propionic acid;
and the corresponding N-oxides, and their prodrugs; and pharmaceutically acceptable salts and solvates (e.g. hydrates) of such compounds and their N-oxides and prodrugs.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention block the interaction of the ligand VCAM-4 to its integrin receptor VLA-4 ($\alpha 4\beta 1$) according to tests described in the literature and described in vitro and in vivo procedures hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of an inhibitor of $\alpha 4\beta 1$ mediated cell adhesion. For example, compounds of the present invention are useful in the treatment of inflammatory diseases, for example joint inflammation, including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds are useful in the treatment of acute synovitis, autoimmune diabetes, autoimmune encephalomyelitis, collitis, atherosclerosis, peripheral vascular disease, cardiovascular disease, multiple sclerosis, asthma, psoriasis restenosis, myocarditis, inflammatory bowel disease and melanoma cell division in metastasis.

A special embodiment of the therapeutic methods of the present invention is the treating of asthma.

Another special embodiment of the therapeutic methods of the present invention is the treating of joint inflammation.

Another special embodiment of the therapeutic methods of the present invention is the treating of inflammatory bowel disease.

According to a further feature of the invention there is provided a method for the treatment of a human or animal patient suffering from, or subject to, conditions which can be ameliorated by the administration of an inhibitor of the interaction of the ligand VCAM-1 to its integrin receptor VLA-4 ($\alpha 4\beta 1$), for example conditions as hereinbefore described, which comprises the administration to the patient of an effective amount of compound of the invention or a composition containing a compound of the invention. "Effective amount" is meant to describe an amount of compound of the present invention effective in inhibiting the interaction of the ligand VCAM-1 to its integrin receptor VLA-4 ($\alpha 4\beta 1$), and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebuliser or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of formula (I) wherein Het, $R^1$, $R^2$, $L^1$, $L^2$ and $Z^1$ are as hereinbefore defined, and Y is carboxy may be prepared by hydrolysis of esters of formula (I) wherein Het, $R^1$, $R^2$, $L^1$, $L^2$ and $Z^1$ are as hereinbefore defined and where the Y is a —$CO_2R^{13}$ group (in which $R^{13}$ is alkyl, alkenyl or arylalkyl). The hydrolysis may conveniently be carried out by alkaline hydrolysis using a base, such as an alkali metal hydroxide, e.g. lithium hydroxide, or an alkali metal carbonate, e.g. potassium carbonate, in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example compounds of formula (I) wherein Het, $R^1$, $R^2$, $L^1$, $L^2$ and $Z^1$ are as hereinbefore defined, and Y is carboxy may be prepared by acid catalysed removal of the tert-butyl group of tert-butyl esters of formula (I) wherein Het, $R^1$, $R^2$, $L^1$, $L^2$ and $Z^1$ are as hereinbefore defined and Y is a —$CO_2R^{13}$ group (in which $R^{13}$ is tert-butyl), using standard reaction conditions, for example reaction with trifluoroacetic acid at a temperature at about room temperature.

As another example compounds of formula (I) wherein Het, $R^1$, $R^2$, $L^1$, $L^2$ and $Z^1$ are as hereinbefore defined and Y is carboxy may be prepared by hydrogenation of compounds of formula (I) wherein Het, $R^1$, $R^2$, $L^1$, $L^2$ and $Z^1$ are as hereinbefore defined and Y is a —$CO_2R^{13}$ group (in which $R^{13}$ is benzyl). The reaction may be carried out in the presence of ammonium formate and a suitable metal catalyst, e.g. palladium, supported on an inert carrier such as carbon, preferably in a solvent such as methanol or ethanol and at a temperature at about reflux temperature. The reaction may alternatively be carried out in the presence of a suitable metal catalyst, e.g. platinum or palladium optionally supported on an inert carrier such as carbon, preferably in a solvent such as methanol or ethanol.

Esters of formula (I) wherein Het, $R^1$, $R^2$, $L^2$ and $Z^1$ are as hereinbefore defined $L^1$ is a —$R^6$—$R^7$— linkage (in which $R^6$ is as hereinbefore defined and $R^7$ is —C(=O)—$NR^5$—) and Y is a —$CO_2R^{13}$ group (in which $R^{13}$ is as hereinbefore defined) may be prepared by reaction of compounds of formula (II):

$R^1Z^1$-Het-$R^6$—C(=O)—$X^1$ \hfill (II)

wherein Het, $R^1$, $R^6$ and $Z^1$ are as hereinbefore and $X^1$ is a hydroxy group or a halogen, preferably chlorine, atom, with amines of formula (III):

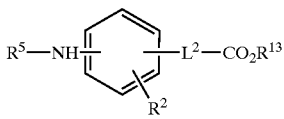

(III)

wherein $R^5$, $R^2$, $R^{13}$ and $L^2$ are as hereinbefore defined. When $X^1$ is a hydroxy group the reaction may be carried out using standard peptide coupling procedures for example coupling in the presence of O-(7-azabenzotriazol-1-yl)-1,1,3,3-tetramethyluronium hexafluorophosphate and triethylamine (or diisopropylethylamine) in tetrahydrofuran (or dimethylformamide), at room temperature. When $X^1$ is a halogen atom the acylation reaction may be carried out with the aid of a base, such pyridine, preferably in a solvent such as tetrahydrofuran and at a temperature at about room temperature.

Esters of formula (I) wherein Het, $R^1$, $R^2$, $L^2$ and $Z^1$ are as hereinbefore defined $L^1$ is a —$R^6$—$R^7$— linkage [in which $R^6$ is as hereinbefore defined, and $R^7$ is —$NR^5$—C(=O)— (where $R^5$ is as hereinbefore defined)] and Y is a —$CO_2R^{13}$ group (in which $R^{13}$ is as hereinbefore defined) may be prepared by reaction of compounds of formula (IV):

$R^1Z^1$-Het-$R^6$—$NHR^5$ (IV)

wherein Het, $R^1$, $R^5$, $R^6$ and $Z^1$ are as hereinbefore, with compounds of formula (V):

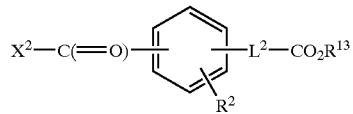

(V)

wherein $R^2$, $R^{13}$ and $L^2$ are as hereinbefore defined and $X^2$ is a hydroxy group or a halogen, preferably chlorine, atom, using procedures described hereinbefore for coupling acids or acid halides with amines.

Esters of formula (I) wherein Het, $R^1$, $R^2$, $L^2$ and $Z^1$ are as hereinbefore defined, $L^1$ is a —$R^6$—$R^7$— linkage (in which $R^6$ is as hereinbefore defined and $R^7$ is —O—) and Y is a —$CO_2R^{13}$ group (in which $R^{13}$ is as hereinbefore defined) may be prepared by reaction of compounds of formula (VI):

$R^1Z^1$-Het-$R^6$—OH (VI)

wherein Het, $R^1$, $R^6$ and $Z^1$ are as hereinbefore defined with compounds of formula (VII):

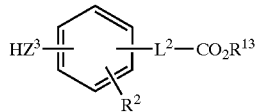

(VII)

wherein $R^2$, $R^{13}$ and $L^2$ are as hereinbefore defined and $Z^3$ is O, in the presence of a dialkyl azodicarboxylate, such as diethyl azodicarboxylate, and triphenylphosphine, preferably in a dry ethereal solvent, e.g. diethyl ether or tetrahydrofuran, preferably at or near room temperature.

Alternatively esters of formula (I) wherein Het, $R^1$, $R^2$, $L^2$ and $Z^1$ are as hereinbefore defined, $L^1$ is a —$R^6$—$R^7$— linkage (in which $R^6$ is as hereinbefore defined and $R^7$ is —O—) and Y is a —$CO_2R^{13}$ group (in which $R^{13}$ is as hereinbefore defined) may be prepared by alkylation of compounds of formula (VII), wherein $R^2$, $R^{13}$ and $L^2$ are as hereinbefore defined and $Z^3$ is O with the appropriate alkyl bromides of formula (VIII):

$R^1Z^1$-Het-$R^6$—$X^3$ (VIII)

Het, $R^1$, $R^6$ and $Z^1$ are as hereinbefore defined and $X^3$ is a halogen, preferably bromo, atom using standard alkylation conditions. The alkylation may for example be carried out in the presence of a base, such as an alkali metal carbonate, e.g. potassium carbonate, or alkali metal hydride, e.g. sodium hydride, in dimethylformamide, or dimethyl sulphoxide, at a temperature from about 0° C. to about 100° C.

Esters of formula (I) wherein Het, $R^1$, $R^2$, $L^2$ and $Z^1$ are as hereinbefore defined, $L^1$ is a —$R^6$—$R^7$— linkage (in which $R^6$ is as hereinbefore defined and $R^7$ is —S—) and Y is a —$CO_2R^{13}$ group (in which $R^{13}$ is as hereinbefore defined) may be similarly prepared by alkylation of compounds of formula (VII) wherein $R^2$, $R^{13}$ and $L^2$ are as hereinbefore defined and $Z^3$ is S.

Esters of formula (I) wherein Het, $R^1$, $R^2$, $L^2$ and $Z^1$ are as hereinbefore defined, $L^1$ is a —$R^6$—$R^7$— linkage [in which $R^6$ is as hereinbefore defined and $R^7$ is —$NR^5$— (where $R^5$ is as hereinbefore defined)] and Y is a —$CO_2R^{13}$ group (in which $R^{13}$ is as hereinbefore defined) may be similarly prepared by alkylation of compounds of formula (III), wherein $R^2$, $R^5$, $R^{13}$ and $L^2$ are as hereinbefore defined.

Esters of formula (I) wherein Het, $R^1$, $R^2$, $L^2$ and $Z^1$ are as hereinbefore defined, $L^1$ is a —$R^6$—$R^7$— linkage [in which $R^6$ is alkylene and $R^7$ is —C(=O)—] and Y is a —$CO_2R^{13}$ group (in which $R^{13}$ is as hereinbefore defined) may be prepared by reaction of acid chlorides of formula (II) wherein Het, $R^1$ and $Z^1$ are as hereinbefore defined, $X^1$ is chloro and $R^6$ is alkylene, with compounds of formula (IX):

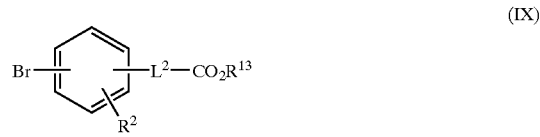

(IX)

wherein $R^2$, $R^3$ and $L^2$ are as hereinbefore defined, by the application or adaptation of the methodology described by R. D. Rieke et al, Synth. Commun., 1995, 23, pages 3923–3930.

Esters of formula (I) wherein Het, $R^1$, $R^2$, $L^2$ and $Z^1$ are as hereinbefore defined, $L^1$ is a —$R^6$—$R^7$— linkage [in which $R^6$ is as hereinbefore defined and $R^7$ is —$NR^5$—C(=O)—NH— (where $R^5$ is as hereinbefore defined)] and Y is a —$CO_2R^{13}$ group (in which $R^{13}$ is as hereinbefore defined) may be prepared by reaction of compounds of formula (IV) wherein Het, $R^1$, $R^5$, $R^6$ and $Z^1$ are as hereinbefore defined, with isocyanates of formula (X):

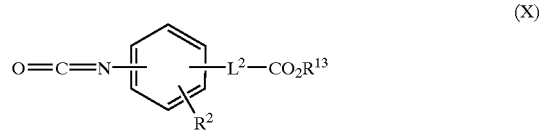

(X)

wherein $R^2$, $R^{13}$ and $L^2$ are as hereinbefore defined. The reaction is preferably carried out with the aid of a base, such as a tertiary amine, for example triethylamine, preferably in a solvent such as dichloromethane, and at a temperature at about room temperature.

Esters of formula (I) wherein Het, $R^1$, $R^2$, $L^2$ and $Z^1$ are as hereinbefore defined, $L^1$ is a —$R^6$—$R^7$— linkage [in which $R^6$ is as hereinbefore defined and $R^7$ is —NH—C(=O)—$NR^5$— (where $R^5$ is as hereinbefore defined)] and Y is a —$CO_2R^{13}$ group (in which $R^{13}$ is as hereinbefore defined) may be similarly prepared by reaction of amines of formula (In) wherein $R^2$, $R^5$, $R^{13}$ and $L^2$ are as hereinbefore defined with compounds of formula (XI):

(XI)

wherein Het, $R^1$, $R^6$ and $Z^1$ are as hereinbefore defined.

Esters of formula (I) wherein Het, $R^1$, $R^2$, $L^2$ and $Z^1$ are as hereinbefore defined, $L^1$ is a —$R^6$—$R^7$— linkage [in which $R^6$ is as hereinbefore defined and $R^7$ is —$SO_2$—$NR_5$— (where $R^5$ is as hereinbefore defined)] and Y is a —$CO_2R^{13}$ group (in which $R^{13}$ is as hereinbefore defined) may be prepared by reaction of compounds of formula (XII):

(XII)

wherein Het, $R^1$, $R^6$ and $Z^1$ are as hereinbefore defined, with amines of formula (IE) wherein $R^2$, $R^5$, $R^{13}$ and $L^2$ are as hereinbefore defined. The reaction is preferably carried out with the aid of a base, such as a tertiary amine, for example triethylamine, preferably in a solvent such as tetrahydrofuran and at a temperature at about room temperature.

Esters of formula (I) wherein Het, $R^1$, $R^2$, $L^1$, $L^2$ and $Z^1$ are as hereinbefore defined, $L^1$ is a —$R^6$—$R^7$— linkage [in which $R^6$ is as hereinbefore defined and $R^7$ is —$NR^5$—$SO_2$— (where $R^5$ is as hereinbefore defined)] and Y is a —$CO_2R^{13}$ group (in which $R^{13}$ is as hereinbefore defined) may be similarly prepared by reaction of compounds of formula (IV) wherein Het, $R^1$, $R^6$, $R^5$ and $Z^1$ are as hereinbefore defined with sulphonyl chlorides of formula (XM):

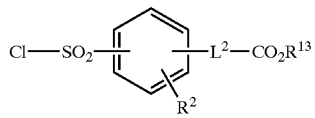
(XIII)

wherein $R^2$, $R^{13}$ and $L^2$ are as hereinbefore defined.

Esters of formula (I) wherein Het, $R^1$, $R^2$, $L^2$ and $Z^1$ are as hereinbefore defined, $L^1$ is a —$R^6$—$R^7$— linkage [in which $R^6$ is as hereinbefore defined and $R^7$ is —O—C(=O)—] and Y is a —$CO_2R^{13}$ group (where $R^{13}$ is as hereinbefore defined) may be prepared by 0-acylation of compounds of formula (VI) wherein Het, $R^1$, $R^6$, and $Z^1$ are as hereinbefore defined with compounds of formula (V) wherein $R^2$, $R^{13}$ and $L^2$ are as hereinbefore defined and $X^2$ is a chlorine atom. The reaction may be carried using standard O-acylation conditions, for example reaction in the presence of a base, such as triethylamine or pyridine, at a temperature from about 0° C. to about room temperature.

Esters of formula (1) wherein Het, $R^1$, $R^2$, $L^2$ and $Z^1$ are as hereinbefore defined, $L^1$ is a —$R^6$—$R^7$— linkage [in which $R^6$ is as hereinbefore defined and $R^7$ is —C(=O)—O—] and Y is a —$CO_2R^{13}$ group (where $R^{13}$ is as hereinbefore defined) may be similarly prepared by O-acylation of compounds of formula (VII) wherein $R^2$, $R^{13}$ and $L^2$ are as hereinbefore defined and $Z^3$ is 0 with compounds of formula (II) wherein Het, $R^1$, $R^6$ and $Z^1$ are as hereinbefore defined and $X^1$ is a chlorine atom.

Esters of formula (I) wherein Het, $R^1$, $R^2$, $L^1$, $L^2$ and $Z^1$ are as hereinbefore defined, $L^1$ is a —$R^6$—$R^7$— linkage (in which $R^6$ is as hereinbefore defined and $R^7$ is —O—C(=O)—NH—) and Y is a —$CO_2R^{13}$ group (where $R^{13}$ is as hereinbefore defined) may be prepared by reaction of compounds of formula (VI) wherein Het, $R^1$, $R^6$ and $Z^1$ are as hereinbefore defined with isocyanates of formula (XI) wherein $R^2$, $R^{13}$ and $L^2$ are as hereinbefore defined The reaction is preferably carried out with the aid of a base, such as a tertiary amine, for example triethylamine, preferably in a solvent such as dichloromethane, and at a temperature at about room temperature.

Esters of formula (1) wherein Het, $R^1$, $R^2$, $L^1$, $L^2$ and $Z^1$ are as hereinbefore defined, $L^1$ is a —$R^6$—$R^7$— linkage (in which $R^6$ is as hereinbefore defined and $R^7$ is —NH—C(=O)—O—] and Y is a —$CO_2R^{13}$ group (where $R^{13}$ is as hereinbefore defined) may be similarly prepared by reaction of isocyanates of formula (XI) wherein Het, $R^1$, $R^6$ and $Z^1$ are as hereinbefore defined with compounds of formula (VII) wherein $R^2$, $R^{13}$ and $L^2$ are as hereinbefore defined and $Z^3$ is O.

Esters of formula (I) wherein Het, $R^1$, $R^2$, $L^2$ and $Z^1$ are as hereinbefore defined, $L^1$ is a —$R^6$—$R^7$— linkage (in which $R^7$ is a direct bond and $R^6$ is a straight or branched chain $C_{2-6}$alkenylene chain where the carbon—carbon double bond is directly attached to the phenyl ring containing the —$L^2$—$CO_2R^{13}$ group) may be prepared by reaction of compounds of formula (XIV):

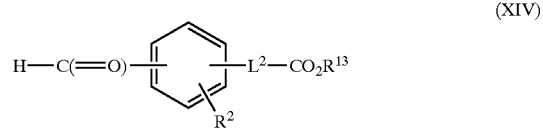
(XIV)

wherein $R^2$, $R^{13}$ and $L^2$ are as hereinbefore defined, with an appropriate phosphorane (or phosphonate ester) of formula (XV):

(XV)

wherein Het, $R^1$ and $Z^1$ are as hereinbefore defined, $R^6$ is a straight or branched chain $C_{1-5}$alkylene chain and $X^5$ is =$PPh_3^+Br^-$ (or —P(=O)(OEt)$_2$), using standard Wittig (or Horner-Wadsworth-Emmons) coupling procedures (for example those described in Tetrahedron Organic Chemistry Series Volume 11, Organic Synthesis Based On Name Reactions and Unnamed reactions, Editors, J. E. Balwin and P. D. Magnus, pages 181 and 421).

Esters of formula (I), wherein Het, $R^1$, $R^2$, $L^1$ and $Z^1$ are as hereinbefore defined, Y is —$CO_2R^{13}$ and $L^2$ is an alkylene linkage substituted by —$NY^3Y^4$ (in which one of $Y^3$ and $Y^4$ is hydrogen and the other is alkyl, or alkyl substituted by alkoxy, aryl, cyano, cycloalkyl, heteroaryl, heterocycloalkyl, hydroxy, oxo, —$NY^1Y^2$, or one or more —$CO_2R^8$ or —C(=O)—$NY^1Y^2$ groups), may be prepared by reaction of esters of formula (I), wherein Het, $R^1$, $R^2$, $L^1$ and $Z^1$ are as hereinbefore defined, Y is —$CO_2R^{13}$ and $L^2$ is an alkylene linkage substituted by —$NH^2$, with aldehydes of formula (XVI):

(XVI)

wherein $R^{14}$ is hydrogen or alkyl, or alkyl substituted by alkoxy, aryl, cyano, cycloalkyl, heteroaryl, heterocycloalkyl, hydroxy, oxo, —$NY^1Y^2$, or one or more —$CO_2R^8$ or —C(=O)—$NY^1Y^2$ groups in the presence of sodium cyanoborohydride. The reaction may be conveniently carried out in methanol, optionally in the presence of sodium acetate and 4A molecular sieves, and at a temperature at about room temperature.

Esters of formula (I), wherein Het, $R^1$, $R^2$, $L^1$ and $Z^1$ are as hereinbefore defined, Y is —$CO_2R^{13}$ and $L^2$ contains a —N($R^8$)—C(=O)—$R^9$ group, may be prepared by reaction of amines of formula (I), wherein Het, $R^1$, $R^2$, $L^1$ and $Z^1$ are as hereinbefore defined, Y is —$CO_2R^{13}$ and $L^2$ contains a —NH($R^8$) group, with compounds of formula (XVII):

$$R^9—C(=O)—X^5 \qquad (XVII)$$

wherein $R^9$ is as hereinbefore defined and $X^5$ is a hydroxy group or a halogen, preferably chlorine, atom. When $X^5$ is a hydroxy group the reaction may be carried out using standard peptide coupling procedures as described hereinbefore. When $X^5$ is a halogen atom the reaction may be carried out with the aid of a base, such pyridine, preferably in a solvent such as tetrahydrofuran and at a temperature at about room temperature.

Esters of formula (I), wherein Het, $R^1$, $R^2$, $L^1$ and $Z^1$ are as hereinbefore defined Y is —$CO_2R^{13}$ and $L^2$ contains a —N($R^8$)—C(=O)—$OR^9$ group, may be prepared by reaction of amines of formula (I), wherein Het, $R^1$, $R^2$, $L^1$ and $Z^1$ are as hereinbefore defined, Y is —$CO_2R^{13}$ and $L^2$ contains a —NH($R^8$) group, with the appropriate chloroformate, e.g. ethyl (or benzyl) chloroformate compounds, according to standard reaction conditions.

Esters of formula (I), wherein Het, $R^1$, $R^2$, $L^1$ and $Z^1$ are as hereinbefore defined Y is —$CO_2R^{13}$ and $L^2$ contains a —N($R^8$)—$SO_2$—$R^9$ group, may be prepared by reaction of amines of formula (I), wherein Het, $R^1$, $R^2$, $L^1$ and $Z^1$ are as hereinbefore defined, Y is —$CO_2R^{13}$ and $L^2$ contains a —NH($R^8$) group, with the appropriate sulphonyl chloride, e.g. an aryl(or heteroaryl)sulphonyl chloride, such as phenyl (or pyridyl)sulphonyl chloride, according to standard reaction conditions.

Esters of formula (I), wherein Het, $R^1$, $R^2$, $L^1$ and $Z^1$ are as hereinbefore defined Y is —$CO_2R^{13}$ (in which $R^{13}$ is alkyl) and $L^2$ is a

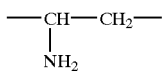

linkage, may be prepared by hydrogenation of esters of formula (I), wherein Het, $R^1$, $R^2$, $L^1$ and $Z^1$ are as hereinbefore defined, Y is —$CO_2R^{13}$ (in which $R^{13}$ is alkyl) and $L^2$ is a

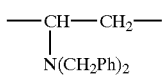

linkage. The reaction may be carried out in the presence of formic acid and a suitable metal catalyst, e.g. palladium, supported on an inert carrier such as carbon, at a temperature at about 60° C. The reaction may conveniently be carried out in the presence of a suitable metal catalyst, e.g. platinum or palladium optionally supported on an inert carrier such as carbon, preferably in a solvent such as methanol or ethanol.

Esters of formula (I), wherein Het, $R^1$, $R^2$, $L^1$ and $Z^1$ are as hereinbefore defined Y is —$CO_2R^{13}$ (in which $R^{13}$ is alkyl) and $L^2$ is a

linkage, may be similarly prepared by hydrogenation of esters of formula (I), wherein Het, $R^1$, $R^2$, $L^1$ and $Z^1$ are as hereinbefore defined, Y is —$CO_2R^{13}$ (in which $R^{13}$ is alkyl) and $L^2$ is a

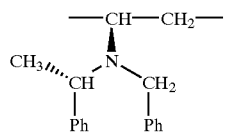

linkage.

Esters of formula (I), wherein Het, $R^1$, $R^2$, $L^1$ and $Z^1$ are as hereinbefore defined Y is —$CO_2R^{13}$ and $L^2$ is a

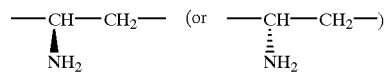

linkage, may also be obtained following standard recrystallisation of salts of the racemic mixture, for example recrystallisation of the tartrate salt.

Esters of formula (I), wherein Het, $R^1$, $R^2$, $L^1$ and $Z^1$ are as hereinbefore defined Y is —$CO_2R^{13}$ and $L^2$ is a

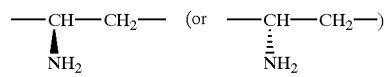

linkage, may also be obtained by the application of standard enzymatic resolution procedures for example those described by Soloshonok, V. A., et. al., Tetrahedron: Asymmetry 6(1995) 7, 1601–1610.

Esters of formula (I) wherein Het, $R^1$, $R^2$, $L^1$ and $Z^1$ are as hereinbefore defined Y is —$CO_2R^{13}$ and $L^2$ is a

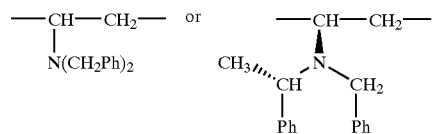

linkage, may be prepared by reaction of compounds of formula (XIII):

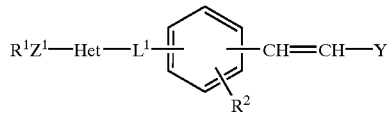

(XVIII)

wherein Het, $R^1$, $R^2$, $L^1$ and $Z^1$ are as hereinbefore defined and Y is —$CO_2R^{13}$, with an alkali metal hydride, such as sodium hydride, in an inert solvent, e.g. tetrahydrofuran, and at a temperature at about room temperature, and subsequent reaction with the anion derived from treating dibenzylamine, or (S)-N-benzyl-α-methylbenzylamine, with butyllithium, at a temperature at about −78° C.

In a process A compounds of formula (I), containing an amide bond may be prepared by coupling of an acid (or an acid halide) with an amine to give an amide bond using standard peptide coupling procedures as described hereinafter.

As an example of process A, compounds of formula (I) wherein $R^1$, $R^2$, $Z^1$ and Het are as hereinbefore defined, $L^1$ represents —$R^6$—$R^7$— (in which $R^6$ is as hereinbefore defined and $R^7$ is —C(=O)—NH—), $L^2$ contains a —N($R^8$)—C(=O)—$R^9$ group (in which $R^8$ and $R^9$ are as hereinbefore defined) and Y is carboxy may be prepared by
(i) treating bromo-Wang resin (4-bromomethylphenoxylated styrene/divinylbenzene copolymer) with an acid of formula (XXI) wherein $R^2$ is as hereinbefore defined and $L^2$ contains a —$N(R^8)$—$R^{15}$ group in which $R^{15}$ is a suitable imino-protecting group, such as 9H-fluoren-9-ylmethoxylcarbonyl, in the presence of a tertiary amine, such as diisopropylethylamine, and cesium iodide, in an inert solvent, such as dimethylformamide, at a temperature at about room temperature, to give Resin 1 wherein $R^2$ is as hereinbefore defined, $L^2$ contains a —$N(R^8)$—$R^{15}$ group (in which $R^{15}$ is as just defined) and

represents the polymeric core comprising polystyrene crosslinked with 1% to 2% divinylbenzene;

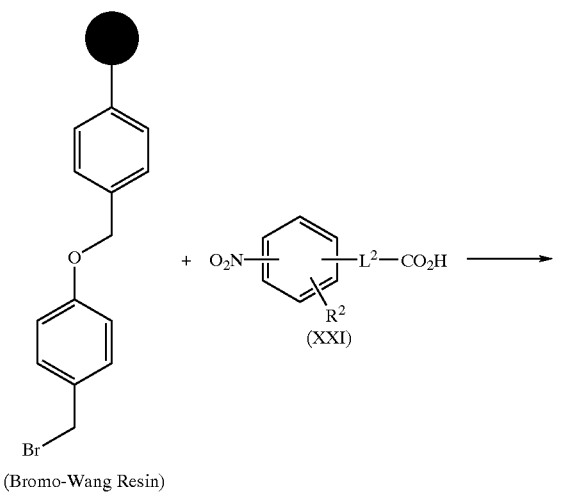

(ii) treatment of Resin 1 in which $L^2$ contains a —$N(R^8)$—$R^{15}$ group with piperidine in an inert solvent, such as dimethylformamide, and at a temperature at about room temperature to give Resin 6 in which $L^2$ contains a —$N(R^8)H$ group;

(iii) reaction of Resin 1 in which $L^2$ contains a —$N(R^8)H$ group with compounds of formula (XVII) wherein $R^9$ and $X^1$ are as hereinbefore defined and is a hydroxy group or a halogen, preferably chlorine, atom to give Resin 1 in which $L^2$ contains a —$N(R^8)$—$C(=O)$—$R^9$ group [When $X^1$ is a hydroxy group the reaction may be carried out using standard peptide coupling procedures for example coupling in the presence of O-(7-azabenzotriazol-1-yl)-1,1,3,3-tetramethyluronium hexafluorophosphate and triethylamine (or dulsopropylethylamine) in tetrahydrofuran (or dimethylformamide), at room temperature. When $X^1$ is a halogen atom the acylation reaction may be carried out with the aid of a base, such pyridine, preferably in a solvent such as tetrahydrofuran and at a temperature at about room temperature];

(iv) treatment of Resin 1 in which $L^2$ contains a —$N(R^7)$—$C(=O)$—$R^8$ group with a solution of tin (II) chloride in dimethylformamide to give Resin 2 wherein $R^2$ and

are as hereinbefore defined and $L^2$ contains a —$N(R^8)$—$C(=O)$—$R^9$ group (in which $R^8$ and $R^9$ are as hereinbefore defined);

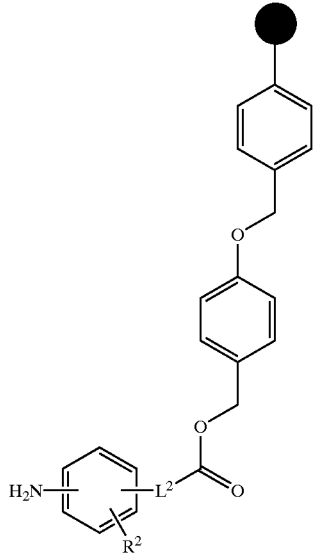

(Resin 2)

(v) reaction of Resin 2 with acids of formula (II) wherein $R^1$, $R^6$, $Z^1$ and Het is as hereinbefore defined, $X^1$ is hydroxy, using peptide coupling conditions, for example those described hereinbefore, to give Resin 3 wherein $R^1$, $R^2$, $R^6$, $Z^1$, Het and are as hereinbefore defined and $L^2$ contains a —$N(R^8)$—$C(=O)$—$R^9$ group (in which $R^8$ and $R^9$ are as hereinbefore defined);

(Resin 3)

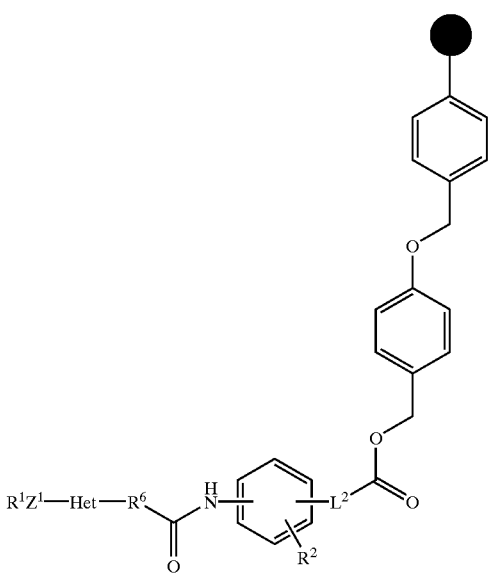

(vi) treatment of Resin 3 with trifluoroacetic acid in an inert solvent, such as dichloromethane, and at a temperature at about room temperature.

According to a further feature of the present invention, compounds of the invention may be prepared by interconversion of other compounds of the invention.

For example compounds of formula (I) wherein Het, $R^1$, $R^2$, $L^1$, $L^2$ and $Z^1$ are as hereinbefore defined and Y is —C(=O)—NHOH, may be prepared by reaction of compounds of formula (I) wherein Het, $R^1$, $R^2$, $L^1$, $L^2$ and $Z^1$ are as hereinbefore defined and Y is carboxy, with hydroxylamine using standard peptide coupling procedures such as treatment with a carboduimide, for example dicyclohexylcarbodiimide, in the presence of triethylamine, in an inert solvent such as dichloromethane or tetrahydrofuran and at a temperature at about room temperature. The coupling may also be carried out using 1-hydroxybenzotriazole and 1-(3-dimethylaminopropyl)-3-ethylcarbodiimide in dichloromethane at room temperature. The preparation may also be carried out using an O-protected hydroxylamine such as O-(trimethylsilyl)hydroxylamine, O-(t-butyldimethylsilyl)-hydroxylamine, or O-(tetrahydropyranyl)hydroxylamine followed by treatment with acid.

As another example of the interconversion process, compounds of formula (I) wherein Het, $R^1$, $R^2$, $L^1$, $Z^1$ and Y are as hereinbefore defined and $L^2$ is an optionally substituted alkylene linkage, may be prepared by hydrogenation of the corresponding compounds of formula (I) in which $L^2$ is the corresponding optionally substituted alkenylene linkage. The hydrogenation may be carried out using hydrogen (optionally under pressure) in the presence of a suitable metal catalyst, e.g. platinum or palladium optionally supported on an inert carrier such as carbon, preferably in a solvent such as methanol or ethanol, and at a temperature at about room temperature.

As another example of the interconversion process, compounds of formula (I) wherein Het, $R^1$, $R^2$, $L^2$, $Z^1$ and Y are as hereinbefore described and $L^1$ is a —$R^6$—$R^7$— linkage where $R^6$ is a straight or branched chain $C_{2-6}$alkylene chain and $R^7$ is a direct bond, may be similarly prepared by hydrogenation of the corresponding compounds of formula (I) in which $L^1$ is a —$R^6$—$R^7$— linkage where $R^6$ is a straight or branched chain $C_{2-6}$alkenylene chain and $R^7$ is a direct bond.

As another example of the interconversion process, compounds of the invention containing a heterocyclic group wherein the hetero atom is a nitrogen atom may be oxidised to their corresponding N-oxides. The oxidation may conveniently be carried out by means of reaction with a mixture of hydrogen peroxide and an organic acid, e.g. acetic acid, preferably at or above room temperature, for example at a temperature of about 60–90° C. Alternatively, the oxidation may be carried out by reaction with a peracid, for example peracetic acid or m-chloroperoxybenzoic acid, in an inert solvent such as chloroform or dichloromethane, at a temperature from about room temperature to reflux, preferably at elevated temperature. The oxidation may alternatively be carried out by reaction with hydrogen peroxide in the presence of sodium tungstate at temperatures between room temperature and about 60° C.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (1) hereinabove. Such isomers can be separated from their mixtures, by the application or adaptation of known methods, for example chromatographic techniques and recrystallisation techniques, or they are separately prepared from the appropriate isomers of their intermediates.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxan, tetrahydrofuran or methanol.

According to a further feature of the invention, base addition salts of the compounds of this invention may be prepared by reaction of the free acid with the appropriate base, by the application or adaptation of known methods.

For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for example methods as described in the Reference Examples or their obvious chemical equivalents.

Acids of formula (II) wherein Het is

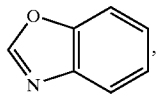, $R^1$ and $R^6$ are as hereinbefore defined, $Z^1$ is NH and $X^1$ is hydroxy may be prepared by reaction of compounds of formula

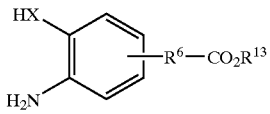 (XIX)

wherein $R^6$ and $R^{13}$ are as hereinbefore defined, and X is O, with isothiocyanates of formula $R^1$—N=C=S in ethanol and at room temperature, followed by reaction with a carbodiimide, such as dicyclohexylcarbodiimide or diisopropylcarbodiimide in ethanol and at a temperature from about room temperature to about reflux temperature, and subsequent conversion of the ester group to an acid group (for example when $R^{13}$ is alkyl by hydrolysis using standard conditions, as described hereinbefore).

Acids of formula (II) wherein Het is

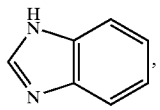, $R^1$ and $R^6$ are as hereinbefore defined, $Z^1$ is NH and $X^1$ is hydroxy may be similarly prepared from compounds of formula (XIX) wherein $R^6$ and $R^{13}$ are as hereinbefore defined and X is NH.

Acid chlorides of formula (II) wherein Het, $R^1$, $R^6$ and $Z^1$ are as hereinbefore defined and $X^1$ is a chlorine atom may be prepared from the corresponding acids of formula (II) wherein Het, $R^1$, $R^6$ and $Z^1$ are as hereinbefore defined and $X^1$ is hydroxy, by the application of standard procedures for the conversion of acids to acid chlorides for example by reaction with oxalyl chloride.

Acid chlorides of formula (V) wherein $R^2$, $R^{13}$ and $L^2$ are as hereinbefore defined and $X^2$ is a chlorine atom may be similarly prepared from the corresponding acids of formula (V) wherein $R^2$, $R^{13}$ and $L^2$ are as hereinbefore defined and $X^2$ is hydroxy.

Compounds of formula (III) wherein $R^2$, $R^{13}$ and $L^2$ are as hereinbefore defined and $R^5$ is methyl may be prepared by treatment of the corresponding compounds of formula (RI) wherein $R^2$, $R^{13}$ and $L^2$ are as hereinbefore defined and $R^5$ is hydrogen with formic acetic anhydride followed by reduction with lithium aluminium hydride according to the procedure described by L. G. Humber L G et al, J Med Chem, 1971, 14, page 982.

Compounds of formula (IV) wherein Het, $R^1$, $R^6$ and $Z^1$ are as hereinbefore defined and $R^5$ is methyl may be similarly prepared by reacting compounds of formula (IV) wherein Het, $R^1$, $R^6$ and $Z^1$ are as hereinbefore defined and $R^5$ is hydrogen.

Compounds of formula (III) wherein $R^2$, $R^{13}$, $L^2$ and $R^5$ are as hereinbefore defined may be prepared by reaction of compounds of formula (XX):

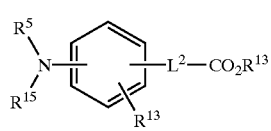 (XX)

wherein $R^2$, $R^{13}$, $L^2$ and $R^5$ are as hereinbefore defined and $R^{15}$ is an acid-labile protecting group, such as tertiary-butyloxycarbonyl, with trifluoroacetic acid, in an inert solvent, such as dichloromethane and at a temperature at about room temperature. This method is particularly suitable for the preparation of compounds of formula (III) where $R^5$ is methyl.

Compounds of formula (III) wherein $R^2$, $R^{13}$ and $L^2$ are as hereinbefore defined and $R^5$ is hydrogen may be prepared by reduction of the corresponding nitro compounds of formula (XXI):

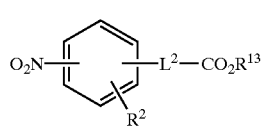 (XXI)

wherein $R^2$, $R^{13}$ and $L^2$ are as hereinbefore defined. The reduction may be carried out using iron powder and ammonium chloride, in aqueous ethanol at a temperature at about reflux.

Compounds of formula (XIX) wherein $R^6$ and $R^{13}$ are as hereinbefore defined and X is NH may be similarly prepared by reduction of the corresponding nitro-amino compounds or dinitro compounds.

Compounds of formula (IV) wherein Het, $R^1$, $R^6$ and $Z^1$ are as hereinbefore defined and $R^5$ is hydrogen may be prepared by reaction of compounds of formula (VIU) wherein Het, $R^1$, $R^6$ and $Z^1$ are as hereinbefore defined and $X^3$ is bromo with phthalimide potassium salt in dimethylformamide followed by reaction with hydrazine hydrate in ethanol (for example using the conditions described by O. Diouf et al., Heterocycles, 1995, 41, page 1219–1233).

Compounds of formula (VI) wherein Het, $R^1$ and $Z^1$ are as hereinbefore defined and $R^6$ is methylene (or a $C_{2-6}$straight or branched alkylene chain), may be prepared by reduction of esters of formula (XXII):

$$R^1Z^1\text{-Het-}R^{16}\text{—}CO_2R^{13} \quad (XXII)$$

wherein Het, $R^1$ and $Z^1$ are as hereinbefore defined, $R^{13}$ is alkyl and $R^{16}$ is a direct bond (or a $C_{1-5}$straight or branched alkylene chain). The reduction may conveniently be carried out with diisobutylaluminium hydride in an inert solvent, such as tetrahydrofuran, at a temperature from about −78° C. to about room temperature. The reduction may also be carried out with lithium aluminium hydride in an inert solvent, such as an ether, for example diethyl ether, at a temperature from about room temperature to about reflux.

Compounds of formula (VII) wherein $R^2$, $R^{13}$ and $L^2$ are as hereinbefore defined and $Z^3$ is O may be prepared from the corresponding acids of formula (XXIII):

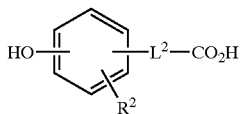

(XXIII)

wheren $R^2$ and $L^2$ are as hereinbefore defined and $Z^3$ is O, by standard esterification procedures for example reaction with a lower alkyl alcohol (e.g. methanol) in the presence of an acid catalyst, such as hydrogen chloride or sulphuric acid.

Compounds of formula (VIII) wherein Het, $R^1$ and $Z^1$ are as hereinbefore defined, $R^6$ is an alkylene chain and $X^3$ is bromo may be prepared by reaction of compounds of formula (VI) wherein Het, $R^1$ and $Z^1$ are as hereinbefore defined, $R^6$ is an alkylene chain with phosphorus tribromide in an inert solvent such as carbon tetrachloride and at a temperature at about room temperature.

Compounds of formula (X) wherein $R^2$, $R^{13}$ and $L^2$ are as hereinbefore defined may be prepared from compounds of formula (III) wherein $R^2$, $R^{13}$ and $L^2$ are as hereinbefore defined and $R^5$ is hydrogen with phosgene following standard reaction conditions for the conversion of amines to isocyanates.

Compounds of formula (XI) wherein Het, $R^1$, $R^6$ and $Z^1$ are as hereinbefore defined may be similarly prepared from compounds of formula (IV) wherein Het, $R^1$, $R^6$ and $Z^1$ are as hereinbefore defined and $R^5$ is hydrogen.

Compounds of formula (XII) wherein Het, $R^1$, $R^6$ and $Z^1$ are as hereinbefore defined may be prepared from compounds of formula (VIR) wherein Het, $R^1$, $R^6$ and $Z^1$ are as hereinbefore defined and $X^3$ is bromo by reaction with sodium sulphite followed by phosphorus trichloride according to the described by P. N. Culshaw and J. C. Walton, J. Chem Soc, Perkin Trans II, 1991, 8, pages 1201–1208.

Compounds of formula (XII) wherein $R^2$, $R^{13}$ and $L^2$ are as hereinbefore defined may be prepared from compounds of formula (HI) wherein $R^2$, $R^{13}$ and $L^2$ are as hereinbefore defined and $R^5$ is hydrogen by standard procedures for the conversion of anilines to the corresponding phenylsulphonyl chlorides.

Compounds of formula (XV) wherein Het, $R^1$ and $Z^1$ are as hereinbefore defined, $R^6$ is a straight or branched chain $C_{1-5}$alkylene chain and $X^5$ is $=PPh_3^+Br^-$ may be prepared by reaction of compounds of formula (VIII) wherein Het, $R^1$ and $Z^1$ are as hereinbefore defined, $R^6$ is a straight or branched chain $C_{1-5}$alkylene chain and $X^3$ is a bromine atom by reaction with triphenylphosphine in an inert solvent and at a temperature from about room temperature to about reflux temperature of the solvent.

Compounds of formula (XX) wherein Het, $R^1$, $R^{11}$ and $Z^1$ are as hereinbefore defined and $R^9$ is alkyl may be similarly prepared from the corresponding acids.

Compounds of formula (X) wherein $R^2$, $R^9$ and $L^2$ are as hereinbefore defined may be prepared from bromo-iodobenzene by the adaptation of procedures described by Y. Tamaru et al, Tetrahedron Letters, 1985, 26, page 5559 and 1986, 27, page 955.

Compounds of formula (XX) wherein $R^2$, $R^{13}$ are as hereinbefore defined, $R^5$ is methyl, $R^{15}$ is an acid-labile protecting group, such as tertiary-butyloxycarbonyl, and $L^2$ is an alkylene linkage substituted by $-NY^3Y^4$ (in which one of $Y^3$ and $Y^4$ is hydrogen and the other is alkyl, or alkyl substituted by alkoxy, aryl, cyano, cycloalkyl, heteroaryl, heterocycloalkyl, hydroxy, oxo, $-NY^1Y^2$, or one or more $-CO_2R^8$ or $-C(=O)-NY^1Y^2$ groups), may be prepared by reaction of compounds of formula (XX) wherein $R^2$, $R^5$, $R^{13}$ and $R^{15}$ are as defined immediately above, and $L^2$ is an alkylene linkage substituted by $-NH_2$, with aldehydes of formula (XVI) wherein $R^{14}$ is as hereinbefore defined in the presence of sodium cyanoborohydride.

Compounds of formula (XX) wherein $R^2$, $R^{13}$ and $R^5$ are as hereinbefore defined, $R^{14}$ is an acid-labile protecting group, such as tertiary-butyloxycarbonyl, and $L^2$ contains a $-N(R^8)-C(=O)-R^9$ group, may be prepared by reaction of compounds of formula (XX) wherein $R^2$, $R^5$, $R^{13}$ and $R^{15}$ are as defined immediately above, and $L^2$ contains a $-NH(R^8)$ group, with compounds of formula (XVII) wherein $R^9$ is as hereinbefore defined and $X^5$ is a hydroxy group or a halogen, preferably chlorine, atom, using standard coupling procedures as described hereinbefore.

Compounds of formula (XX) wherein $R^2$, $R^{13}$ and $R^5$ are as hereinbefore defined, $R^{15}$ is an acid-labile protecting group, such as tertiary-butyloxycarbonyl, and $L^2$ contains a $-N(R^8)-C(=O)-OR^9$ group, may be prepared by reaction of compounds of formula (XX) wherein $R^2$, $R^5$, $R^{13}$ and $R^{15}$ are as defined immediately above, and $L^2$ contains a $-NH(R^8)$ group, with Boc-anhydride, according to standard reaction conditions.

Compounds of formula (XX) wherein $R^2$, $R^{13}$ and $R^5$ are as hereinbefore defined, $R^{15}$ is an acid-labile protecting group, such as tertiary-butyloxycarbonyl, and $L^2$ contains a $-N(R^8)-SO_2-R^9$ group, may be prepared by reaction of compounds of formula (XX) wherein $R^2$, $R^5$, $R^{13}$ and $R^{15}$ are as defined immediately above, and $L^2$ contains a $-NH(R^8)$ group, with the appropriate sulphonyl chloride, e.g. an aryl (or heteroaryl) sulphonyl chloride, such as phenyl (or pyridyl) sulphonyl chloride, according to standard reaction conditions.

Compounds of formula (XX) wherein $R^2$, $R^{13}$ and $R^5$ are as hereinbefore defined, $R^{15}$ is an acid-labile protecting group, such as tertiary-butyloxycarbonyl, and $L^2$ is a

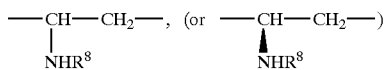

linkage, may be prepared by hydrogenation of compounds of formula (XX) wherein $R^2$, $R^5$, $R^{13}$ and $R^{15}$ are as defined immediately above, and $L^2$ is a

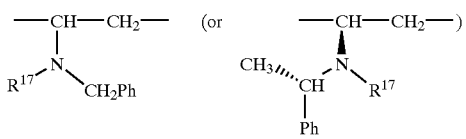

linkage where $R^{17}$ is $R^8$ or benzyl, using procedures described hereinbefore.

Compounds of formula (XX) wherein $R^2$, $R^{13}$ and $R^5$ are as hereinbefore defined, $R^{15}$ is an acid-labile protecting group, such as tertiary-butyloxycarbonyl, and $L^2$ is a

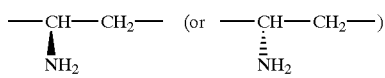

linkage, may also be obtained following standard recrystallisation of salts of the racemic mixture or enzymatic resolution procedures, for example those described hereinbefore.

Compounds of formula (XX) wherein $R^2$, $R^{13}$ and $R^5$ are as hereinbefore defined, $R^{15}$ is an acid-labile protecting group, such as tertiary-butyloxycarbonyl, and $L^2$ is a

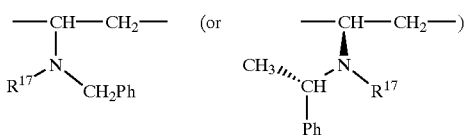

linkage, where $R^{17}$ is as defined hereinbefore, may be prepared by reaction of compounds of formula (XXIV):

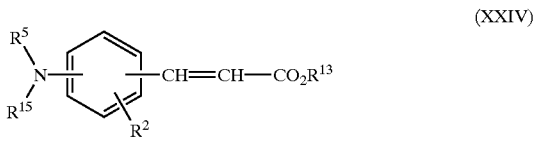

wherein $R^2$, $R^5$, $R^{13}$ and $R^{15}$ are as hereinbefore defined, with an alkali metal hydride, such as sodium hydride, in an inert solvent, e.g. tetrahydrofuran, and at a temperature at about room temperature, and subsequent reaction with the anion derived from treating the appropriate amine, such as dibenzylamine, (S)-N-methyl-c-methylbenzylamine or (S)-N-benzyl-α-methylbenzylamine, using procedures described hereinbefore.

Compounds of formula (XXIV), wherein $R^2$, $R^5$, $R^{13}$ and $R^{15}$ are as hereinbefore defined may be prepared by reaction of compounds of formula (XXV):

wherein $R^2$, $R^5$ and $R^{15}$ are as hereinbefore defined, with an acrylic acid ester, such as tert-butyl acrylate, in the presence of palladium acetate, a triarylphosphine, such as tri(2-methylphenyl)phosphine, and a tertiary amine, such as tributylamine, in an inert solvent, such as dimethylformamide and at a temperature up to about 100° C.

Compounds of formula (XXV) wherein $R^2$, $R^5$ and $R^{15}$ are as hereinbefore defined, may be prepared by the application or adaption of procedures described by Ciattini et al, Tetrahedron Letters, 1995, 36, pages 4133–4136.

Intermediates of formulae (Resin 1), (Resin 2) and (Resin 3) are novel compounds and, as such, they and their processes described herein for their preparation constitute further features of the present invention.

The present invention is further Exemplified but not limited by the following illustrative Examples and Reference Examples.

High Pressure Liquid Chromatography (HPLC) conditions for determination of retention times (RT) were: 15 cm Hypersil Elite C-18 column, ELS detector; solvent acetonitrile/water gradient (both buffered with 0.5% trifluoroacetic acid): 20% acetonitrile for 3 minutes; than ramp up to 80% over the next 12 minutes; maintain at 80% acetonitrile for 3 minutes; then ramp back to 20% acetonitrile over 0.5 minutes (total run time 20 minutes).

EXAMPLE 1

[R] 3-(Acetyl-methyl-amino)-3-(4-{methyl-[(2-o-tolylamino-benzoxazol-6-yl)-acetyl]-amino}-phenyl)-propionic Acid A solution of 2-o-tolylamino-benzoxazol-6-ylacetic acid (200mg, Reference Example 1) and diisopropylethylamine (260 mg) in dimethylformamide (5 mL) was treated successively with O-(7-azabenzotriazol-1-yl)-1,1,3,3-tetramethyluronium hexafluorophosphate (300 mg) and then with [R]-tert-butyl 3-(acetylmethylamino)3-[(4-methylamino)phenyl]propionate (250 mg, Reference Example 4). After stirring at room temperature for 2 hours the mixture was partitioned between ethyl acetate (100 mL) and hydrochloric acid (100 mL, 1 M). The organic layer was washed with aqueous sodium bicarbonate solution (5%), then dried and then evaporated. The residue was subjected to flash chromatography on silica eluting with ethyl acetate to give a colourless gum (240 mg) which was dissolved in trifluoroacetic acid. After standing at room temperature for 2 hours the mixture was evaporated and the residue was triturated with ether to give the title compound (100 mg) as a colourless foam. HPLC: RT=11.45 minutes (92%). MS(ES negative): 513 M⁻.

EXAMPLE 2

(R,S) 3-Benzoylamino-3-{4-[2-(2-o-tolylamino-benzoxazol-6-yl)-acetylamino]-phenyl}-propionic Acid Step 1: A suspension of Bromo-Wang resin (6.9 g, Novabiochem, 1 mmol/g) in the minimum volume of dimethylformamide (about 25 mL) was treated with (RS) 3-(9H-fluoren-9-ylmethoxycarbonylamino)-3-(4-nitro-phenyl)-propionic acid (3.71 g), then with caesium iodide (1.78 g), and then with diisopropylethylamine (1.5 mL). The mixture was allowed to shake gently at room temperature overnight. The resin was drained and then washed (i) three times with dimethylformamide, (ii) twice with methanol, (iii) three times with tetrahydrofuran, (iv) once with methanol, and (v) once with dichloromethane.

Step 2: The resin from step 1 was treated with a mixture of piperidine and dimethylformamide (30 mL, 1:4, v/v) at room temperature for 2 hours. The resin was drained and then washed (i) three times with dimethylformamide, (ii) once with methanol, (iii) once with tetrahydrofuran, (iv) once with methanol, and (v) once with dichloromethane and then dried at room temperature under vacuum.

Step 3: A suspension of the resin from step 2 (615 mg) in dimethylformamide (2 mL) was treated successively with O-(7-azabenzotriazol-1-yl)-1,1,3,3-tetramethyluronium hexafluorophosphate (630 mg), a solution of benzoic acid (200 mg) in dimethylformamide (1 mL) and diisopropylethylamine (0.58 mL). After standing at room temperature for 4 hours with occasional agitation the resin was drained and then washed (i) four times with dimethylformamide, (ii) once with methanol, (iii) once with tetrahydrofuran, (iv) once with methanol, (v) once with dichloromethane and (vi) once with ether and then dried at room temperature under vacuum. A small portion of this resin (20 mg) was treated with a mixture of trifluoroacetic acid and dichloromethane (1:1, v/v) at room temperature for about 45 minutes followed by filtration and evaporation of the filtrate to give (R,S) 3-Benzoylamino-3-(4-nitrophenyl)-propionic acid. HPLC: $R_T$=13.3 minutes (97% by UV@200 nM). MS: 315 (MH⁺).

Step 4: The Resin from step 3 (325 mg) was treated with a solution of tin (II) chloride in dimethylformamide (3 mL, 2M). After standing at room temperature with occasional agitation for 7 hours the resin was drained and then washed (i) three times with dimethylformamide, (ii) twice with methanol, and (iii) three times with dimethylformamide. The resin was resuspended in dimethylformamide (5 mL) and then treated successively with O-(7-azabenzotriazol-1-yl)-1,1,3,3-tetramethyluronium hexafluorophosphate (350 mg), (2-o-tolylamino-benzoxazol-6-yl)-acetic acid (250 mg), and diisopropylethylamine (0.32 mL). This mixture was allowed to stand at room temperature overnight. The resin was drained and then washed (i) three times with dimethylformamide, (ii) twice with methanol, and (iii) three times with tetrahydrofuran, (iv) once with methanol and once with dichloromethane.

Step 5. The Resin from step 4 was treated with a mixture of trifluoroacetic acid and dichloromethane (5 mL, 1:1, v/v) and the mixture allowed to stand at room temperature with occasional agitation for 1 hour. The resin was then drained and the filtrate was evaporated. The residue was triturated with water to give a yellow solid, which was recrystallised from aqueous ethanol to give the title compound (50 mg) as an off-white solid. HPLC: $R_T$=14.0 minutes (80% by UV@220 nM). MS: 549(MH$^+$).

EXAMPLE 3

(R) 3-[(5-Methyl-isoxazole-3-carbonyl)-amino]-3-{4-[2-(2-o-tolylamino-benzoxazol-6-yl)-acetylamino]-phenyl}-propionic Acid A solution of (2-o-tolylamino-benzoxazol-6-yl)-acetic acid (245 mg, Reference Example 1), (R) 3-(4-amino-phenyl)-3-[(5-methyl-isoxazole-3-carbonyl)-amino]-propionic acid tert-butyl ester (300 mg, Reference Example 10) and O-(7-azabenzotriazol-1-yl)-1,1,3,3-tetramethyluronium hexafluorophosphate (360 mg) in dimethylformamide (10 mL) was treated with diisopropylethylamine (260 mg). After standing at room temperature for 3 hours the mixture was partitioned between ethyl acetate (10 mL) and acetic acid (100 mL, 2M). The organic phase was washed with sodium hydrogen carbonate solution (100 mL, 5% w/v) then dried and then evaporated. The residue was subjected to flash chromatography on silica eluting with a mixture of ethyl acetate and cyclohexane (1:1, v/v). The material obtained was treated with a mixture of trifluoroacetic acid and dichloromethane (10 mL, 1:1, v/v). The mixture was kept at room temperature for 2 hours and then evaporated. The residue was triturated with ether to give the title compound (230 mg) as a white amorphous powder.

EXAMPLE 4

4-(2-Carboxy-1-{4-[2-(2-o-tolylamino-benzoxazol-5-yl)-acetylamino]-phenyl}-ethylcarbamoyl)-butyric Acid A mixture of methyl 4-(2-methoxycarbonyl-1-{4-[2-(2-o-tolylamino-benzoxazol-5-yl)-acetylamino]-phenyl}-ethylcarbamoyl)-butyrate (0.31 g, Reference Example 12) aqueous sodium hydroxide solution (2.64 ml, 1M) and tetrahydrofuran was heated at reflux temperature for 3 hours. The mixture was then treated with a further aliquot of aqueous sodium hydroxide solution (2.64 ml, 1M) and heating at reflux temperature was continued for a further 3 hours. The reaction mixture was evaporated and the residue was dissolved in water. The pH of this solution was adjusted to 1–2 by addition of concentrated 1,57 hydrochloric acid. The resulting solid was filtered, then washed well with water, then dried and then recrystallised from aqueous iso-butanol. The crystalline solid was washed with pentane and then dried at 100° C. under vacuum to give the title compound (0.13 g) as colourless crystals, m.p. 255.6–257.1° C. [Elemental analysis: Found: C, 64.51; H, 5.41; N, 10.03; H$_2$O, 1.58%. Calculated for C$_{30}$H$_{30}$N$_4$O$_7$.0.5H$_2$O: C, 63.43; H, 5.51; N, 9.87; H$_2$O, 1.59%].

EXAMPLE 5

(a) (R,S) 3-(4-{2-[2-(2-Methyl-phenylamino)-benzoxazol-6-yl]-acetylamino}-phenyl)-3-[(5-methylisoxazole-3-carbonyl)-amino]-propionic Acid Step 1. 4-(Bromomethyl)phenoxymethyl polystyrene (10 g, 1.0 mmol/g) was swollen in dimethylformamide for 30 minutes and then drained. (40 ml) was added with N,N-diisopropylethylamine (2.5 ml), cesium iodide (2.85 g) and N-(9-fluorenylmethoxycarbonyl)-3-amino-3-(4-nitrophenyl)-propionic acid (5.94 g). The mixture was agitated overnight, drained and the resin was washed with excess dimethylformamide, then with dichloromethane, then with diethyl ether and then dried under vacuum.

Step 2. The resin from Step 1 (2 g) was then swollen in dimethylformamide for 30 minutes and then drained. A solution of piperidine in dimethylformamide (20% v/v; 20 ml) was then added and the resin agitated for 2 minutes and then drained. A second portion of piperidine in dimethylformamide (20% v/v; 20 ml) was then added and the resin agitated for 2 minutes, drained and the resin washed with excess dimethylformamide.

Step 3. Dimethylformamide (15 ml) was added to the resin from Step 2 together with N,N-diisopropylethylamine (1.29 g), 5-methylisoxazole-3-carboxylic acid (0.57 g) and O-(7-azabenzotriazole-yl)-N,N,N',N'-tetramethyluronium hexafluorophosphate (1.71 g). The mixture was agitated overnight and then the resin was drained, then washed with (i) excess dimethylformamide, (ii) dichloromethane, (iii) diethyl ether and then dried under vacuum.

Step 4. The resin (1.5 g) from Step 3 was then swollen in dimethylformamide for 30 minutes, then drained and then treated with a solution of anhydrous tin (ii) chloride in dimethylformamide (2M, 15 ml). The mixture was agitated for 7 hours and then drained. The resin was washed with (i) excess dimethylformamide, (ii) dichloromethane (iii) diethyl ether and then dried under vacuum.

Step 5. The resin (1.0 g) from Step 4 was then swollen in dimethylformamide for 30 minutes and then drained. Dimethylformamide (10 ml) was added to the resin together with N,N-diisopropylethylamine (0.322 g), 4-nitro-(3-acetyloxy)phenylacetic acid (0.233 g) and O-(7-azabenzotriazole-1-yl)-N,N,N',N'-tetramethyluronium hexafluorophosphate (0.38 g). The mixture was agitated for 6 hours. The resin was drained and then washed with excess dimethylformamide.

Step 6. The resin from Step 5 was treated with a solution of piperidine in dimethylformamide (20% v/v; 10 ml). After agitating overnight the resin was drained and then washed with excess dimethylformamide.

Step 7. The resin (1.0 g) from Step 6 was then swollen in dimethylformamide for 30 minutes, then drained and then treated with a solution of anhydrous tin (ii) chloride in dimethylformamide (2M, 15 ml). After agitating for 7 hours the resin was drained and then washed with (i) excess dimethylformamide, (ii) dichloromethane (iii) diethyl ether and then dried under vacuum.

Step 8. The resin (100 mg) from Step 7 was treated with o-tolylisothiocyanate (0.12 g) and dimethylformamide (2 ml). After agitating at 70° C. overnight the resin was drained, then washed with excess dimethylformamide and then treated with dimethylformamide (2 ml) and N,N'-diisopropylcarbodiimide (0.126 g). After agitating at 70° C. overnight the resin was drained, then washed with (i) excess dimethylformamide, (ii) dichloromethane (iii) diethyl ether and then dried under vacuum.

Step 9. The resin from Step 8 was then soaked in trifluoroacetic acid and water (9:1) for 45 minutes. The resin was filtered from the solution and the filtrate was evaporated. The residue was subjected to reverse phase HPLC (gradient:20–80% [aqueous acetonitrile+1% trifluoroacetic acid] over 20 mins). LCMS: $R_T$=4.40 minutes; MS: 555 (M)$^+$, 553(M)$^-$.

(b) By proceeding in a similar manner to Example 5(a) but using 2-methoxyphenyl-isothiocyanate in Step 8 there was prepared (R,S) 3-(4-{2-[2-(2-methoxy-phenylamino)- benzoxazol-6-yl]-acetylamino}-phenyl)-3-[(5-methylisoxazole-3-carbonyl)-amino]-propionic acid. LCMS $R_T$=4.45 minutes; MS: 571(M)$^+$, 569(M)$^-$.

(c) By proceeding in a similar manner to Example 5(a) but using 2-chlorophenyl-isothiocyanate in Step 8 there was prepared (R,S) 3-(4-{2-[2-(2-chloro-phenylamino)-benzoxazol-6-yl]-acetylamino}-phenyl)-3-[(5-methylisoxazole-3-carbonyl)-amino]-propionic acid LCMS $R_T$=4.55minutes; MS: 575(M)$^+$, 573(M)$^-$.

(d) By proceeding in a similar manner to Example 5(a) but using phenylisothiocyanate in Step 8 there was prepared (R,S) 3-(4-{2-[2-(phenylamino)-benzoxazol-6-yl]-acetylamino}-phenyl)-3-[(5-methylisoxazole-3-carbonyl)-amino]-propionic acid. LCMS $R_T$=4.43 minutes; MS: 541 (M)$^+$, 539(M)$^-$.

(e) By proceeding in a similar manner to Example 5(a) but using 2-pyridylisothiocyanate in Step 8 there was prepared (R,S) 3-(4-{2-[2-(2-pyridylamino)-benzoxazol-6-yl]-acetylamino}-phenyl)-3-[(5-methylisoxazole-3-carbonyl)-amino]-propionic acid. LCMS $R_T$=3.83 minutes; MS: 542 (M)$^+$, 540(M)$^-$.

(f) By proceeding in a similar manner to Example 5(a) but using morpholinoacetic acid in Step 3 there was prepared (R,S) 3-(4-{2-[2-(2-methyl-phenylamino)-benzoxazol-6-yl]-acetylamino}-phenyl)-3-[(morpholinoacetyl)-amino]-propionic acid. LCMS $R_T$=3.57 minutes; MS: 572(M)$^+$, 570(M)$^-$.

(g) By proceeding in a similar manner to Example 5(a) but using isonicotinic acid in Step 3 and 2-methoxyphenyl-isothiocyanate in Step 8 there was prepared (R,S) 3-(4-{2-[2-(2-methoxy-phenylamino)-benzoxazol-6-yl]-acetylamino}-phenyl)-3-[(pyridine-4-carbonyl)-amino]-propionic acid. LCMS $R_T$=4.23 minutes; MS: 566(M)$^+$, 564(M)$^-$.

(h) By proceeding in a similar manner to Example 5(a) but using isonicotinic acid in Step 3 and 2-chlorophenyl-isothiocyanate in Step 8 there was prepared (R,S) 3-(4-{2-[2-(2-chloro-phenylamino)-benzoxazol-6-yl]-acetylamino}-phenyl)-3-[(pyridine-4-carbonyl)-amino]-propionic acid. LCMS $R_T$=4.32 minutes; MS: 570(M)$^+$, 568(M)$^-$.

(i) By proceeding in a similar manner to Example 5(a) but using isonicotinic acid in Step 3 and 3-methoxyphenyl-isothiocyanate in Step 8 there was prepared (R,S) 3-(4-{2-[2-(3-methoxy-phenylamino)-benzoxazol-6-yl]-acetylamino}-phenyl)-3-[(pyridine-4-carbonyl)-amino]-propionic acid. LCMS $R_T$=4.23 minutes; MS: 566(M)$^+$, 564(M)$^-$.

(j) By proceeding in a similar manner to Example 5(a) but using isonicotinic acid in Step 3 and phenyl-isothiocyanate in Step 8 there was prepared (R,S) 3-(4-{2-[2-(phenyamino)-benzoxazol-6-yl]-acetylamino}phenyl)-3-[(pyridine-4-carbonyl)-amino]propionic acid. LCMS $R_T$=4.18 minutes; MS: 536(M)$^+$, 534(M)$^-$.

(k) By proceeding in a similar manner to Example 5(a) but using isonicotinic acid in Step 3 and 2pyridylisothiocyanate in Step 8 there was prepared (R,S) 3-(4-{2-[2-(2pyridylamino)-benzoxazol-6-yl]-actylamino}-phenyl)-3-[(pyridine-4-carbonyl)-amino]-propionic acid. LCMS $R_T$=3.42 minutes; MS: 537(M)$^+$, 535(M)$^-$.

(l) By proceeding in a similar manner to Example 5(a) but using thiophene-2-carboxylic acid in Step 3 there was prepared (R,S) 3-(4-{2-[2-(2-methyl-phenylamino)-benzoxazol-6-yl]-aetylamino}-phenyl)-3-[(thiophene-2-carbonyl)-amino]-propionic acid. LCMS $R_T$=4.38 minutes; MS: 555(M)$^+$, 554(M)$^-$.

REFERENCE EXAMPLE 1

2-o-Tolylamino-benzoxazole-6-acetic Acid

A mixture of ethyl 4-amino-3-hydroxy-phenylacetate (3.3 g, Reference Example 2) and o-tolylisothiocyanate (2.5 mL) in ethanol (150 mL) was stirred at room temperature for about 2 hours. After standing at room temperature overnight the mixture was evaporated and the residue was subjected to flash chromatography on silica eluting with a mixture of pentane and ethyl acetate (7:3, v/v) to give a yellow foam. A solution of this material in ethanol (150 mL was treated with dicyclohexylcarbodiimide (3.0 g) and the mixture was heated at reflux temperature for 2 hours. The mixture was evaporated and the residue subjected to short column chromatography on silica eluting with a mixture of 5–10% tert-butyl methyl ether in dichloromethane to remove dicyclohexylurea. The resulting light yellow oil was dissolved in ethanol (100 mL) and the solution was treated with sodium hydroxide solution (15 mL, 1M) then heated at reflux temperature for 2 hours. The reaction mixture was evaporated and the residue was dissolved in water. The solution was washed with ethyl acetate and the aqueous layer was acidified to pH 1 by addition of concentrated hydrochloric acid. The resulting white precipitate was collected by filtration, then washed thoroughly with water, and then dried to give the title compound (1.8 g) as a white solid.

REFERENCE EXAMPLE 2

Ethyl 4-amino-3-hydroxy-phenylacetate

A solution of ethyl 3-hydroxy-4-nitrophenylacetate (5.0 g, Reference Example 3) was dissolved in ethanol (approximately 200 mL) was treated with ammonium formate (approximately 20 g). The mixture was warmed to 50° C. and then treated cautiously with palladium on charcoal (approximately 1 g, 5%)—effervescence was observed. After 30 minutes the mixture was filtered hot through a pad of celite and the filtrate was concentrated to give the title compound (3.3 g) as a black solid.

REFERENCE EXAMPLE 3

Ethyl 3-hydroxy-4-nitrophenylacetate

A solution of 3-hydroxy-4-nitrophenylacetic acid (4.0 g, prepared according to the procedure described by Meyer et al, J. Med. Chem., 1997, 40, pages 1049–1062) in ethanol (approximately 100 ml) was treated with concentrated hydrochloric acid (5–8 drops) was heated at reflux temperature for 3 hours then evaporated. The residue was dissolved in tert-butyl methylether and the solution was washed with saturated aqueous sodium bicarbonate solution, then with water, then dried, and then evaporated to give the title compound (5.0 g) as a light yellow solid.

REFERENCE EXAMPLE 4

[R]-tert-Butyl 3-(acetylmethylamino)-3-[(4-methylamino) phenyl]propionate

[R]-tert-butyl 3-(acetylmethylamino)-3-[(4-(N-tertiary-butyloxycarbonyl-N-methylamino)phenyl]propionate (4.3 g, Reference Example 5) was dissolved in a 5% solution of trifluoroacetic acid in dichloromethane (200 ml) at room temperature and the reaction followed by TLC analysis. When reaction was complete by TLC (about 1.5 hours) the mixture was poured cautiously onto a mixture of dichloromethane (100 mL) and saturated aqueous sodium bicarbonate solution (200 mL). The organic layer was dried and then evaporated to give the title compound (3.9 g) as a yellow oil which slowly crystallised on standing.

REFERENCE EXAMPLE 5
[R]-tert-Butyl 3-(acetylmethylamino)-3-[(4-(N-tertiary-butyloxycarbonyl-N-methylamino)phenyl]propionate A stirred solution of [R]-tert-butyl 3-(methylamino)-3-[(4-(N-tertiary-butyloxycarbonyl-N-methylamino)phenyl] propionate (6.0 g, Reference Example 6) in tetrahydrofuran (100 mL) was treated with triethylamine (5.4 g) and then with acetyl chloride (2.12 g) dropwise (an immediate precipitate was formed). The mixture was stirred for a further 30 minutes, then partitioned between ethyl acetate (200 mL) and hydrochloric acid (100 mL, 1 M). The organic layer was washed with aqueous sodium bicarbonate solution (5%) then dried and then evaporated to give the title compound (4.3 g) as a yellow oil.

REFERENCE EXAMPLE 6
[R]-tert-Butyl 3-(methylamino)-3-[(4-(N-tertiary-butyloxycarbonyl-N-methylamino)phenyl]propionate A solution of tert-butyl 3(R)-[N-methyl-N-((S) 1-phenylethyl)amino]-3-[(4-(N-tertiary-butyloxycarbonyl-N-methylamino)phenyl]propionate (6.5 g, Reference Example 7) in ethanol (50 mL), warmed to 60° C., was treated with formic acid (4 mL) then with 10% palladium on charcoal (2 g). After stirring at 60° C. for one hour the reaction mixture was allowed to cool to room temperature then filtered thorough filter-aid to remove the spent catalyst. The filtrate was evaporated to low bulk and the residue was partitioned between ethyl acetate and aqueous sodium bicarbonate solution (200 mL, 5%). The organic layer was dried and then evaporated to give the title compound (6.0 g) as a colourless oil.

REFERENCE EXAMPLE 7
tert-Butyl 3-(R)-[N-methyl-N-((S) 1-phenylethyl)amino]-3-[(4-(N-tertiary-butyloxycarbonyl-N-methylamino)phenyl] propionate A stirred solution of (S) N-methyl-N-(1-phenylethyl) amine (9.8 g) was dissolved in tetrahydrofuran (60 mL), under a nitrogen atmosphere and cooled to below −70° C., was treated dropwise with a solution of butyllithium in hexanes (11.3 mL, 2.5M). After about 10 minutes the mixture was treated dropwise with a solution of tert-butyl 4-(N-tertiary-butyloxycarbonyl-N-methylamino)cinnamate (4.7 g, Reference Example 8) in tetrahydrofuran (40 mL) over 20 minutes. The reaction mixture was stirred for a further 20 minutes then poured onto a mixture of ethyl acetate (500 mL) and brine (500 mL). The organic layer was dried and then evaporated. The residue was subjected to flash chromatography on silica eluting with a mixture of ethyl acetate and cyclohexane (7:3, v/v) to give the title compound (6.5 g) as a colourless oil.

REFERENCE EXAMPLE 8
tert-Butyl 4-(N-tertiary-butyloxycarbonyl-N-methylamino) cinnamate A mixture of N-tertiary-butyloxycarbonyl-N-methyl4-iodoaniline (11 g, Reference Example 9), tert-butyl acrylate (8.4 g), tris-(o-tolyl)phosphine (500 mg), palladium (II) acetate (150 mg), and triethylamine (7 g) in DMF (20 mL) was stirred at 90° C. under nitrogen overnight. The reaction mixture was cooled to room temperature then partitioned between ethyl acetate (500 mL) and hydrochloric acid solution (500 mL, 1M). The organic phase was dried and then evaporated. The residue was crystallised from cyclohexane to give the title compound (7.4 g) as a white solid.

REFERENCE EXAMPLE 9
N-tertiary-Butyloxycarbonyl-N-methyl-4-iodoaniline

A solution of N-tertiary-butyloxycarbonyl-4-iodoaniline (11.5 g, see P G Ciattini et al, Tet. Lett, 1995, 36, 4133–4136 for preparation) in dimethylformamide (70 mL), under nitrogen, was treated portionwise with sodium hydride (1.6 g, 60% dispersion in mineral oil). When effervescence had ceased (after about 5 minutes) the mixture was treated with methyl iodide and stirring was continued at room temperature for 2 hours. The reaction mixture was partitioned between ethyl acetate (500 mL) and water (500 mL). The organic phase was dried and then evaporated to give the title compound (11.5 g) as a pink oil.

REFERENCE EXAMPLE 10
(a) (R) 3-(4-Amino-phenyl)-3-[(5-methyl-isoxazole-3-carbonyl)-amino]-propionic Acid Tert-Butyl Ester A solution of (R) 3-(4-tert-butoxycarbonylamino-phenyl)-3-[(5-methyl-isoxazole-3-carbonyl)-amino]-propionic acid tert-butyl ester (2 g, Reference Example 11) in dichloromethane (50 mL) was treated with trifluoroacetic acid (5 mL). After four hours [the reaction was monitored by TLC: no more starting material was visible after about 4 hours] at room temperature the reaction mixture was poured carefully onto a mixture of sodium hydrogen carbonate solution (100 mL, 5% w/v) and dichloromethane (50 mL). The organic layer was separated then dried and then evaporated to give the title compound (1.0 g) as a yellow oil which slowly crystallised on standing.

(b) By proceeding in a similar manner to that described in Reference Example 10(a) but using (R) methyl 3-(4-tert-butoxycarbonylamino-phenyl)-3-[4-methoxycarbonyl-butanoyl-amino]-propionate (Reference Example 13) there was prepared (R) methyl 3-(4-amino-phenyl)-3-[4-methoxycarbonylbutanoyl-amino]-propionate as an amber coloured oil.

REFERENCE EXAMPLE 11
(R) 3-(4-tert-Butoxycarbonylamino-phenyl)-3-[(5-methyl-isoxazole-3-carbonyl)-amino]-propionic Acid Tert-Butyl Ester A solution of (R) 3-Amino-3-(4-tert-butoxycarbonylamino-phenyl)-propionic acid tert-butyl ester (2.0 g), 5-methyl-isoxazole-3-carboxylic acid (890 mg), and O-(7-azabenzotriazol-1-yl)-1,1,3,3-tetramethyluronium hexafluorophosphate (2.66 g) in dimethylformamide (20 mL) was treated with diisopropylethylamine (1.8 g). After standing at room temperature for 1 hour the mixture was partitioned between ethyl acetate (100 mL) and hydrochloric acid (100 mL, 1M). The organic layer was washed with sodium hydrogen carbonate solution (100 mL, 5% w/v), then dried and then evaporated. The residue was triturated with the minimum volume of ether to give the title compound (2.0 g) as a white solid.

REFERENCE EXAMPLE 12
Methyl 4-(2-methoxycarbonyl-1-{4-[2-(2-o-tolylamino-benzoxazol-5-yl)-acetylamino]-phenyl}-ethylcarbamoyl)-butyrate A mixture of 2-o-tolylamino-benzoxazole-6-acetic acid (0.5 g, Reference Example 1), O-(7-azabenzotriazol-1-yl)-1,1,3,3-tetramethyluronium hexafluorophosphate (1 g), dimethylformamide (40 mL), diisopropylethylamine (1.5 mL) and (R) methyl 3-(4-amino-phenyl)-3-[4-methoxycarbonylbutanoyl-amino]-propionate [0.57 g, Reference Example 10(a)] was stirred at room temperature for 2.5 hours, then left for 4 days and then evaporated. The residue was dissolved in ethyl acetate and the solution was washed well with water and then evaporated. The resulting yellow foam was subjected to short column chromatography on silica eluting with a mixture of dichloromethane and methanol (19:1, v/v) followed by trituration with ethanol to give the title compound (0.31 g) as a colourless solid.

REFERENCE EXAMPLE 13

(R) Methyl 3-(4-tert-butoxycarbonylamino-phenyl)-3-[4-methoxycarbonylbutanoyl-amino]propionate A solution of (R) 3-Amino-3-(4-tert-butoxycarbonylamino-phenyl)-propionic acid methyl ester (4.5 g) ad triethylamine (2.65 mL) in dichloromethane (35 mL) was treated dropwise with methyl 4-(chloroformyl)butyrate (2.21 mL). After stirring at room temperature for 2 hours the reaction mixture was treated with water and then extracted with ethyl acetate. The extract was washed with water, then dried and then evaporated to give the title compound as an oil which was used without further purification.

In vitro and In vivo Test Procedures

1. Inhibitory Effects of Compounds on VLA-4 Dependent Cell Adhesion to Fibronectin and VCAM.

1.1 Metabolic Labelling of RAMOS Cells.

RAMOS cells (a pre-B cell line from ECACC, Porton Down, UK) are cultured in RPMI culture medium (Gibco, UK) supplemented with 5% foetal calf serum (FCS, Gibco, UK). Prior to assay the cells are suspended at a concentration of $0.5 \times 10^6$ cells/ml RPMI and labelled with 400 $\mu$gCi/100 mls of [$^3$H]-methionine (Amersham, UK) for 18 hours at 37° C.

1.2 96 Well Plate Preparation for Adhesion Assay.

Cytostar plates (Amersham, UK) were coated with 50 $\mu$l/well of either 3 $\mu$g/ml human soluble VCAM-1 (R&D Systems Ltd, UK) or 28.8 $\mu$g/ml human tissue Fibronectin (Sigma, UK). In control non-specific binding wells 50 $\mu$l phosphate buffered saline was added. The plates were then left to dry in an incubator at 25° C., overnight. The next day the plates were blocked with 200 $\mu$l/well of Pucks buffer (Gibco, UK) supplemented with 1% BSA (Sigma, UK). The plates were left at room temperature in the dark for 2 hours. The blocking buffer was then disposed of and the plates dried by inverting the plate and gently tapping it on a paper tissue. 50 $\mu$l/well of 3.6% dimethyl sulphoxide in Pucks buffer supplemented with 5 mM manganese chloride (to activate the integrin receptor Sigma, UK) and 0.2% BSA (Sigma, UK), was added to the appropriate control test binding and non-specific binding assay wells in the plate. 50 $\mu$l/well of the test compounds at the appropriate concentrations diluted in 3.6% dimethyl sulphoxide in Pucks buffer supplemented with 5mM manganese chloride and 0.2% BSA, was added to the test wells.

Metabolically labelled cells were suspended at $4 \times 10^6$ cells/ml in Pucks buffer that was supplemented with manganese chloride and BSA as above. 50 $\mu$l/well of cells in 3.6% dimethyl sulphoxide in Pucks buffer and supplements was added to all plate wells.

The same procedure exists for plates coated with either VCAM-1 or fibronectin and data is determined for compound inhibition of cell binding to both substrates.

1.3 Performance of Assay and Data Analysis.

The plates containing cells in control or compound test wells are incubated in the dark at room temperature for 1 hour.

The plates are then counted on a Wallac Microbeta scintillation counter (Wallac, UK) and the captured data processed in Microsoft Excel (Microsoft, US). The data was expressed as an IC50, namely the concentration of inhibitor at which 50% of control binding occurs. The percentage binding is determined from the equation:

$$\{[(C_{TB}-C_{NS})-(C_I-C_{NS})]/(C_{TB}-C_{NS})\} \times 100 = \% \text{ binding}$$

where $C_{TB}$ are the counts bound to fibronectin (or VCAM-1) coated wells without inhibitor present, $C_{NS}$ are the counts present in wells without substrate, and $C_I$ are the counts present in wells containing a cell adhesion inhibitor.

Compound data of this invention is expressed for IC$_{50}$s for inhibition of cell adhesion to both fibronectin and VCAM-1. Particular compounds of the invention inhibit cell adhesion to fibronectin and VCAM-1 with IC$_{50}$s in the range 100 micromolar to 1 nanomolar. Preferred compounds of the invention inhibit cell adhesion to fibronectin and VCAM-1 with IC$_{50}$s in the range 10 nanomolar to 1 nanomolar.

2. Inhibition of Antigen-Induced Airway Inflammation in the Mouse and Rat.

2.1 Sensitization of the Animals.

Rats (Brown Norway, Harland Olac, UK) are sensitized on days 0, 12 and 21 with ovalbumin (100 $\mu$g, intraperitoneally [i.p], Sigma, UK) administered with aluminium hydroxide adjuvant (100 mg, i.p., Sigma, UK) in saline (1 ml, i.p.).

In addition mice (C57) are sensitized on days 0 and 12 with ovalbumin (10 $\mu$g, i.p.) administered with aluminium hydroxide adjuvant (20 mg, i.p.) in saline (0.2 ml, i.p.).

2.2 Antigen Challenge.

Rats are challenged on any one day between days 28–38, while mice are challenged on any one day between days 20–30.

The animals are challenged by exposure for 30 minutes (rats) or 1 hour (mice) to an aerosol of ovalbumin (10 g/l) generated by an ultrasonic nebulizer (deVilbiss Ultraneb, US) and passed into an exposure chamber.

2.3 Treatment Protocols.

Animals are treated as required before or after antigen challenge. The aqueous-soluble compounds of this invention can be prepared in water (for oral, p.o. dosing) or saline (for intratracheal, i.t. dosing). Non-soluble compounds are prepared as suspensions by grinding and sonicating the solid in 0.5% methyl cellulose/0.2% polysorbate 80 in water (for p.o. dosing, both Merck UK Ltd., UK) or saline (for i.t. dosing). Dose volumes are: for rats 1 ml/kg, p.o. or 0.5 mg/kg, i.t.; for mice 10 ml/kg, p.o. or 1 ml / kg, i.t.

2.4 Assessment of Airway Inflammation.

The cell accumulation in the lung is assessed 24 hours after challenge (rats) or 48–72 hours after challenge (mice). The animals are euthanized with sodium pentobarbitone (200 mg/kg, i.p., Pasteur Merieux, France) and the trachea is immediately cannulated. Cells are recovered from the airway lumen by bronchoalveolar lavage (BAL) and from the lung tissue by enzymatic (collagenase, Sigma, UK) disaggregation as follows.

BAL is performed by flushing the airways with 2 aliquots (each 10 ml/kg) RPMI 1640 medium (Gibco, UK) containing 10% fetal calf serum (FCS, Serotec Ltd., UK). The recovered BAL aliquots are pooled and cell counts made as described below.

Immediately after BAL, the lung vasculature is flushed with RPMI 1640/FCS to remove the blood e pool of cells. The lung lobes are removed and cut into 0.5 mm pieces. Samples (rats: 400 mg; mice: 150 mg) of homogenous lung tissue are incubated in RPMI 1640/FCS with collagenase (20 U/ml for 2 hours, then 60 U/ml for 1 hour, 37° C.) to disaggregate cells from the tissue. Recovered cells are washed in RPMI 1640/FCS.

Counts of total leukocytes recovered from the airway lumen and the lung tissue are made with an automated cell counter (Cobas Argos, US). Differential counts of eosinophils, neutrophils and mononuclear cells are made by light microscopy of cytocentrifuge preparations stained with Wright-Giemza stain (Sigma, UK). T cells are counted by flow cytometry (EPICS XL, Coulter Electronics, US) using fluophore-labelled antibodies against CD2 (a pan-T cell marker used to quantify total T cells), CD4, CD8 and CD25 (a marker of activated T cells). All antibodies were supplied by Serotec Ltd., UK)

2.5 Data Analysis.

The cell data was expressed as mean cell numbers in unchallenged, challenged and vehicle treated, and challenged and compound treated groups, including the standard error of the means. Statistical analysis of the difference among treatment groups was evaluated using one-way analysis of variance via the Mann-Whitney test. Where p<0.05 no statistical significance existed.

What is claimed is:

1. A compound of formula (Ia):

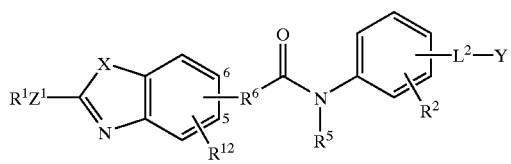

(Ia)

wherein:

R$^1$ represents aryl, heteroaryl, optionally substituted alkyl, alkenyl or alkynyl where each is optionally substituted by R$^3$, —Z$^2$R$^4$, —Z$^3$H, —C(=O)—R$^4$, —NR$^5$—C(=Z$^3$)—R$^4$, —NR$^5$—C(=O)—OR$^4$, —NR$^5$—SO$_2$—R$^4$, —SO$_2$—NY$^1$Y$^2$, —NY$^1$Y$^2$ or —C(=Z$^3$)—NY$^1$Y$^2$; or cycloalkyl or heterocycloalkyl, each optionally substituted by R$^4$, —Z$^2$R$^4$, —Z$^3$H, —C(=O)—R$^4$, —NR$^5$—C(=Z$^3$)—R$^4$, —NR$^5$—C(=O)—OR$^4$, —NR$^5$—SO$_2$—R$^4$, —SO$_2$—NY$^1$Y$^2$, —NY$^1$Y$^2$ or —C(=Z$^3$)—NY$^1$Y$^2$;

R$^2$ represents hydrogen, halogen, C$_{1-4}$alkyl or C$_{1-4}$alkoxy;

R$^3$ represents aryl, cycloalkyl, cycloalkenyl, heteroaryl, or heterocycloalkyl;

R$^4$ represents alkyl, alkenyl, alkynyl, aryl, arylalkyl, arylalkenyl, arylalkynyl, cycloalkyl, cycloalkylalkyl, cycloalkenyl, cycloalkenylalkyl, heteroaryl, heteroarylalkyl, heteroarylalkenyl, heteroarylalkynyl, heterocycloalkyl or heterocycloalkylalkyl;

R$^5$ represents hydrogen or C$_{1-4}$alkyl;

R$^6$ is an alkylene chain, an alkenylene chain or an alkynylene chain;

R$^8$ is hydrogen, alkyl, aryl, arylalkyl, cycloalkyl, cycloalkylalkyl, heteroaryl, heteroarylalkyl, heterocycloalkyl or heterocycloalkylalkyl;

R$^9$ is alkyl, aryl, cycloalkyl, heteroaryl or heterocycloalkyl, or alkyl substituted by aryl, an acidic functional group or corresponding protected derivative, cycloalkyl, heteroaryl, heterocycloalkyl, —Z$^3$H, —Z$^2$R$^4$, —C(=O)—NY$^3$Y$^4$ or —NY$^3$Y$^4$;

R$^{12}$ is hydrogen, acyl, acylamino, alkoxy, alkoxycarbonyl, alkylenedioxy, alkylsulphinyl, alkylsulphonyl, alkylthio, aroyl, aroylamino, aryl, arylalkyloxy, arylalkyloxycarbonyl, arylalkylthio, aryloxy, aryloxycarbonyl, arylsulphinyl, arylsulphonyl, arylthio, carboxy, cyano, halo, heteroaroyl, heteroaryl, heteroarylalkyloxy, heteroaroylamino, heteroaryloxy, hydroxy, nitro, trifluoromethyl, Y$^1$Y$^2$N—, Y$^1$Y$^2$NCO—, Y$^1$Y$^2$NSO$_2$—, Y$^1$Y$^2$N—C$_{2-6}$alkylene-Z—, alkylC(=O)—Y$^1$N—, alkylSO$_2$—Y$^1$N— or alkyl optionally substituted with aryl, heteroaryl, hydroxy, or Y$^1$Y$^2$N—;

L$^2$ represents an alkylene chain substituted by hydroxy, oxo, —OR$^4$, —O—C(=O)—R$^4$, —N(R$^8$)—C(=O)—R$^9$, —N(R$^8$)—C(=O)—OR$^9$, —N(R$^8$)—SO$_2$—R$^9$, or —NY$^3$Y$^4$;

X is O;

Y is carboxy;

Y$^1$ and Y$^2$ are independently hydrogen, alkenyl, alkyl, aryl, arylalkyl, cycloalkyl, heteroaryl or heteroarylalkyl; or the group —NY$^1$Y$^2$ may form a cyclic amine;

Y$^3$ and Y$^4$ are independently hydrogen, alkenyl, alkyl, alkynyl, aryl, cycloalkenyl, cycloalkyl, heteroaryl, heterocycloalkyl, or alkyl substituted by alkoxy, aryl, cyano, cycloalkyl, heteroaryl, heterocycloalkyl, hydroxy, oxo, —NY$^1$Y$^2$, or one or more —CO$_2$R$^8$ or —C(=O)—NY$^1$Y$^2$ groups; or the group —NY$^3$Y$^4$ may form a cyclic amine;

Z$^1$ represents NR$^5$;

Z$^2$ is O or S(O)$_n$;

Z$^3$ is O or S; and n is zero or an integer 1 or 2;

and the corresponding N-oxides, and their prodrugs; and pharmaceutically acceptable salts, and solvates of such compounds and their N-oxides and prodrugs.

2. A compound according to claim 1 in which R$^1$ represents optionally substituted phenyl.

3. A compound according to claim 1 in which Z$^1$ represents NH.

4. A compound according to claim 1 in which R$^6$ is methylene.

5. A compound according to claim 1 in which R$^2$ represents hydrogen, C$_{1-4}$alkyl or C$_{1-4}$alkoxy.

6. A compound according to claim 1 in which R$^2$ represents hydrogen.

7. A compound according to claim 1 in which L$^2$ represents a straight or branched C$_{1-4}$alkylene linkage substituted by —N(R$^8$)—C(=O)—R$^9$, —N(R$^8$)—C(=O)—OR$^9$, —N(R$^8$)—SO$_2$—R$^9$ or —NY$^3$Y$^4$.

8. A compound according to claim 1 in which L$^2$ represents ethylene substituted by —N(R$^8$)—C(=O)—R$^9$, —N(R$^8$)—C(=O)—OR$^9$, —N(R$^8$)—SO$_2$—R$^9$ or —NY$^3$Y$^4$.

9. A compound according to claim 1 in which L$^2$ represents

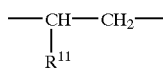

where R$^{11}$ is —N(R$^8$)—C(=O)—R$^9$, —N(R$^8$)—C(=O)—OR$^9$, —N(R$^8$)—SO$_2$—R$^9$, or —NY$^3$Y$^4$.

10. A compound according to claim 1 in which L$^2$ represents

where R$^{11}$ is —N(R$^8$)—C(=O)—R$^9$, —N(R$^8$)—C(=O)—OR$^9$, —N(R$^8$)—SO$_2$—R$^9$, or —NY$^3$Y$^4$.

11. A compound according to claim 1 in which R$^{12}$ represents hydrogen, C$_{1-4}$alkyl or C$_{1-4}$alkoxy.

12. A compound according to claim 1 in which the group

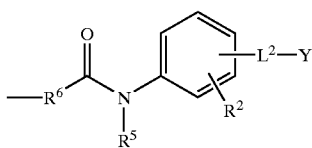

is attached at the ring 6 position.

13. A compound according to claim 1 of the following formula:

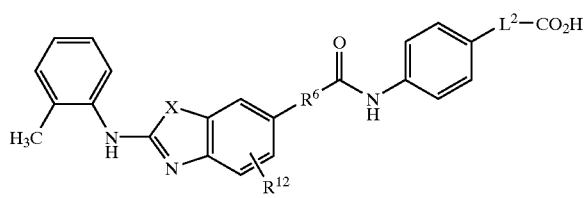

in which $R^{12}$ is selected from hydrogen, $C_{1-4}$alkyl or $C_{1-4}$alkoxy, X is O, $R^6$ is $C_{1-2}$alkylene, and $L^2$ represents a straight or branched $C_{1-4}$alkylene linkage substituted by —N($R^8$)—C(=O)—$R^9$, —N($R^8$)—C(=O)—O$R^9$, —N($R^8$)—SO$_2$—$R^9$ or —N$Y^3Y^4$.

14. A compound according to claim 13 in which $R^{12}$ represents hydrogen, methyl, ethyl or methoxy.

15. A compound according to claim 13 in which $R^6$ represents methylene.

16. A pharmaceutical composition comprising an effective amount of a compound according to claim 1 or a corresponding N-oxide or prodrug, or a pharmaceutically acceptable salt or solvate of such a compound or an N-oxide prodrug thereof, in association with a pharmaceutically acceptable carrier or excipient.

17. A method for the treatment of a human or non-human animal patient suffering from a condition which can be ameliorated by the administration of an inhibitor of α4β1 mediated cell adhesion comprising administering to said patient an effective amount of a compound according to claim 1 or a corresponding N-oxide or prodrug, or a pharmaceutically acceptable salt or solvate of such a compound or an N-oxide or prodrug thereof.

18. A method for the treatment of a patient suffering from asthma comprising administering to said patient an effective amount of a compound according to claim 1 or a corresponding N-oxide or prodrug, or a pharmaceutically acceptable salt or solvate of such a compound or an N-oxide or prodrug thereof.

19. A method for the treatment of a patient suffering from an inflammatory disease comprising administering to said patient an effective amount of a compound according to claim 1 or a corresponding N-oxide or prodrug, or a pharmaceutically acceptable salt or solvate of such a compound or an N-oxide or prodrug thereof.

20. A method for the treatment of a human or non-human animal patient suffering from a condition which can be ameliorated by the administration of an inhibitor of α4β1 mediated cell adhesion comprising administering to said patient an effective amount of a composition according to claim 16.

21. A method for the treatment of a patient suffering from asthma comprising administering to said patient an effective amount of a composition according to claim 16.

22. A method for the treatment of a patient suffering from an inflammatory disease comprising administering to said patient an effective amount of a composition according to claim 16.

* * * * *